US012076708B2

(12) United States Patent
Janjua et al.

(10) Patent No.: US 12,076,708 B2
(45) Date of Patent: *Sep. 3, 2024

(54) METHOD FOR TREATING AN AMMONIUM SALT

(71) Applicant: KING FAHD UNIVERSITY OF PETROLEUM AND MINERALS, Dhahran (SA)

(72) Inventors: Muhammad Ramzan Saeed Ashraf Janjua, Dhahran (SA); Saba Jamil, Dhahran (SA); Shanza Rauf Khan, Dhahran (SA)

(73) Assignee: KING FAHD UNIVERSITY OF PETROLEUM AND MINERALS, Dhahran (SA)

(*) Notice: Subject to any disclaimer, the term of this patent is extended or adjusted under 35 U.S.C. 154(b) by 0 days.

This patent is subject to a terminal disclaimer.

(21) Appl. No.: 18/116,666

(22) Filed: Mar. 2, 2023

(65) Prior Publication Data
US 2023/0201808 A1 Jun. 29, 2023

Related U.S. Application Data

(62) Division of application No. 15/992,950, filed on May 30, 2018, now Pat. No. 11,628,423.

(51) Int. Cl.
*B01J 23/745* (2006.01)
*B01J 35/23* (2024.01)
(Continued)

(52) U.S. Cl.
CPC ............. *B01J 23/745* (2013.01); *B01J 35/23* (2024.01); *B01J 35/50* (2024.01); *B01J 35/51* (2024.01);
(Continued)

(58) Field of Classification Search
CPC . B01J 23/745; B01J 35/51; B01J 35/23; B01J 35/50; B01J 37/08; C01G 49/06; C07C 213/02
See application file for complete search history.

(56) References Cited

U.S. PATENT DOCUMENTS 3,627,471 A 12/1971 Roger et al.
2019/0247524 A1 8/2019 Hou

FOREIGN PATENT DOCUMENTS

CN 104353495 B 4/2016
CN 105754095 A 7/2016
(Continued)

OTHER PUBLICATIONS

Xu, Selective preparation of nanorods and micro-octahedrons of Fe2O3 and their catalytic performances for thermal decomposition of ammonium perchlorate, 2008, Powder Technology, 185, 176-180 (Year: 2008).*

(Continued)

*Primary Examiner* — James A Fiorito
(74) *Attorney, Agent, or Firm* — Oblon, McClelland, Maier & Neustadt, L.L.P.

(57) ABSTRACT

A thermal method of forming ferric oxide nano/microparticles with predominant morphology is described using different solvents. Methods of using the $Fe_3O_4$ nano/microparticles as catalysts in the reduction of nitro compounds with sodium borohydride to the corresponding amines and decomposition of ammonium salts.

13 Claims, 14 Drawing Sheets

(51) Int. Cl.
  *B01J 35/50* (2024.01)
  *B01J 35/51* (2024.01)
  *B01J 37/08* (2006.01)
  *C01G 49/06* (2006.01)
  *C07C 213/02* (2006.01)

(52) U.S. Cl.
  CPC ............ *B01J 37/08* (2013.01); *C01G 49/06* (2013.01); *C07C 213/02* (2013.01); *C01P 2002/72* (2013.01); *C01P 2004/03* (2013.01); *C01P 2004/04* (2013.01); *C01P 2004/34* (2013.01); *C01P 2004/38* (2013.01); *C01P 2004/41* (2013.01); *C01P 2004/61* (2013.01); *C01P 2004/64* (2013.01)

(56) References Cited

FOREIGN PATENT DOCUMENTS

| | | |
|---|---|---|
| CN | 106711429 A | 5/2017 |
| CN | 107096515 A | 8/2017 |

OTHER PUBLICATIONS

Qitong Huang, et al., "Phase and Morphology Controlled in the Synthesis of Iron Oxide Particles: Dimension-based Carbonaceous Materials as Modifier", Electronic Supplementary Material (ESI) for RSC Advances, 2016, pp. 1-6.

Lin Zhuang, et al., "Preparation and Characterization of $Fe^3O_4$ Particles with Novel Nanosheets Morphology and Magnetochromatic Property by a Modified Solvothermal Method", Scientific Reports, vol. 5, No. 9320, Mar. 23, 2015, pp. 1-6.

Qiufeng Yang, et al., "Preparation of Magnetic $Fe_3O_4$ Microspheres Using Different Surfactant and Silica-coated Magnetic Particles" 2015 AASRI International Conference on Industrial Electronics and Applications (IEA 2015), 2015, pp. 47-51.

David Cantillo, et al., "Hydrazine-mediated Reduction of Nitro and Azide Functionalities Catalyzed by Highly Active and Reusable Magnetic Iron Oxide Nanocrystals", Journal of Organic Chemistry, vol. 78, No. 9, Apr. 5, 2013, pp. 4530-4542.

Eunice Aparecida Campos, et al., "Synthesis, Characterization and Applications of Iron Oxide Nanoparticles—a Short Review", J. Aerosp. Technol. Manag., São José dos Campos, Jul.-Sep. 2015, pp. 267-276.

* cited by examiner

Figures 2a  Figure 2b  Figure 2c
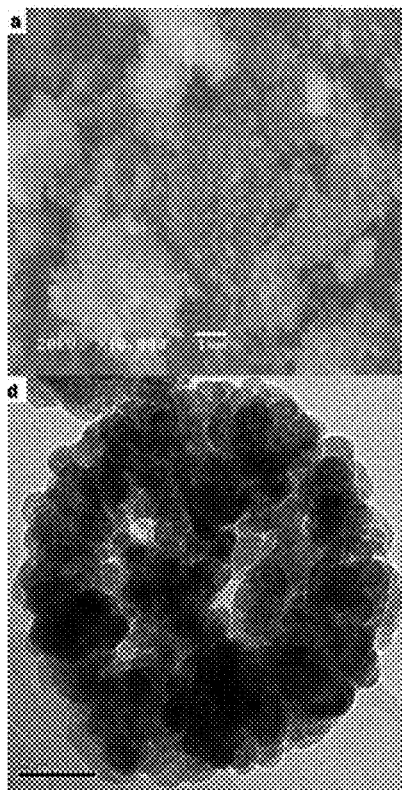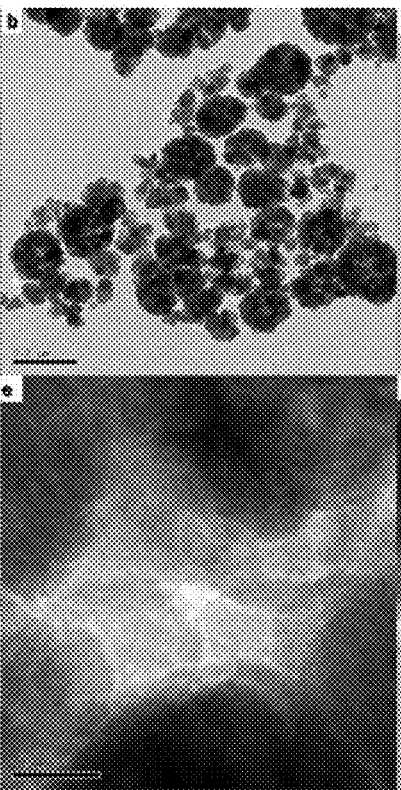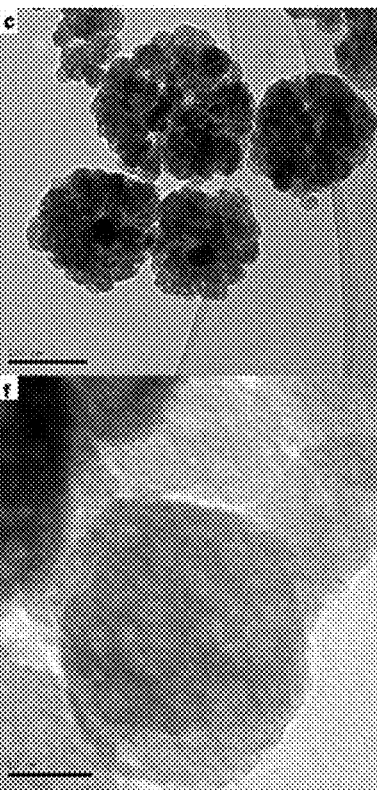
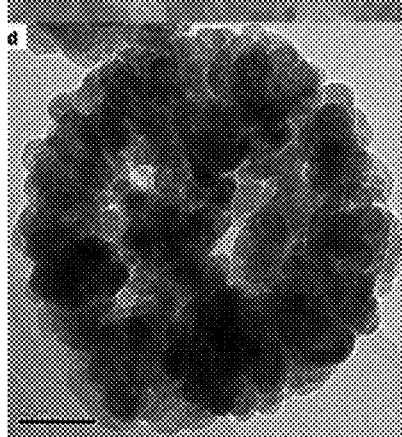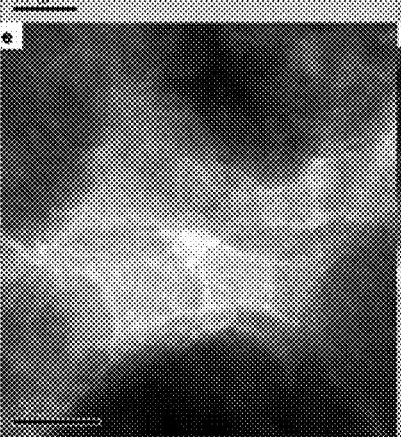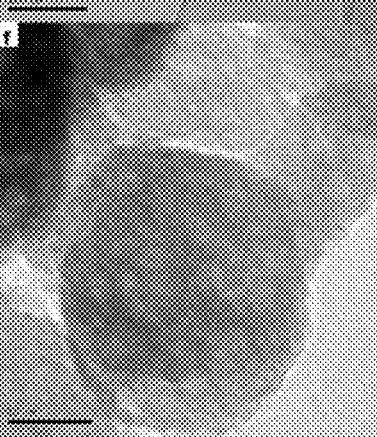
Figures 2d  Figure 2e  Figure 2f Figure 5a
Figure 5b
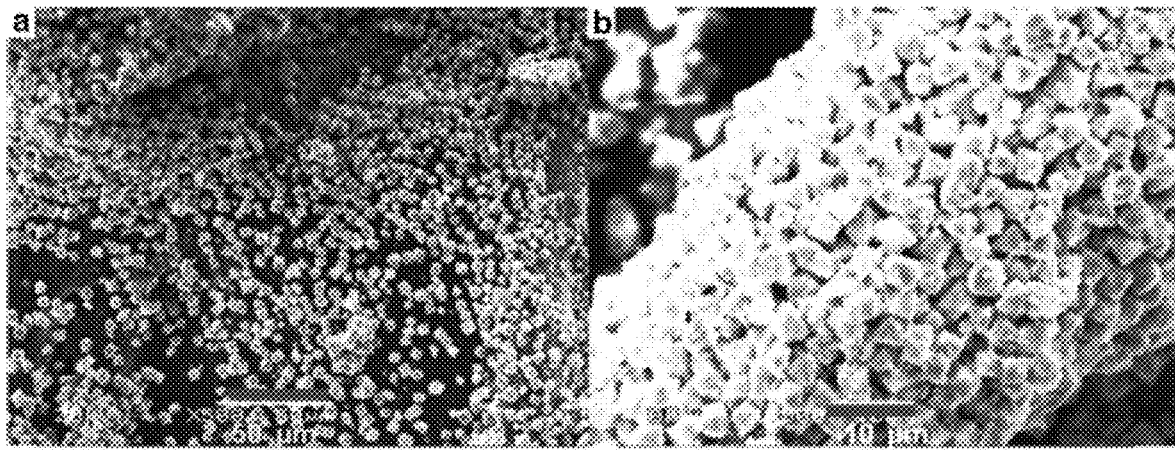
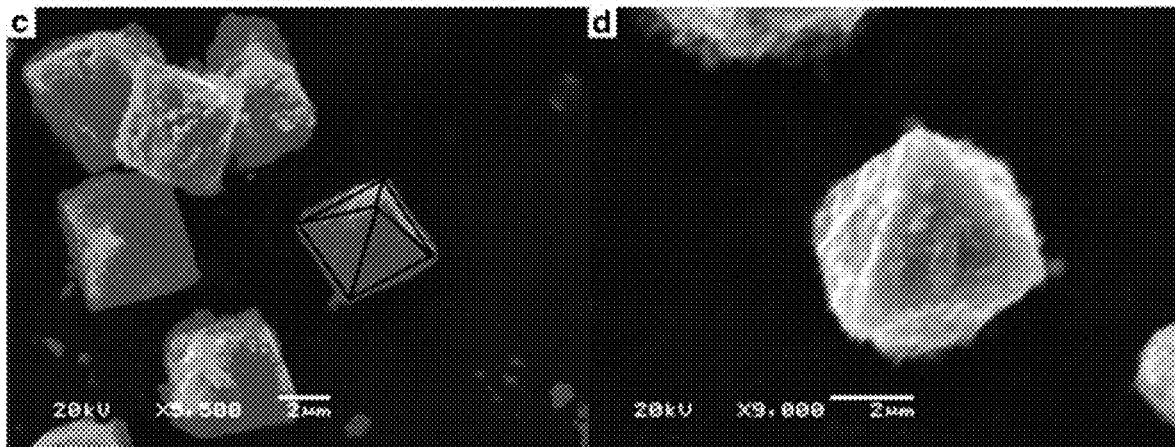
Figure 5c
Figure 5d Figure 6a
Figure 6b
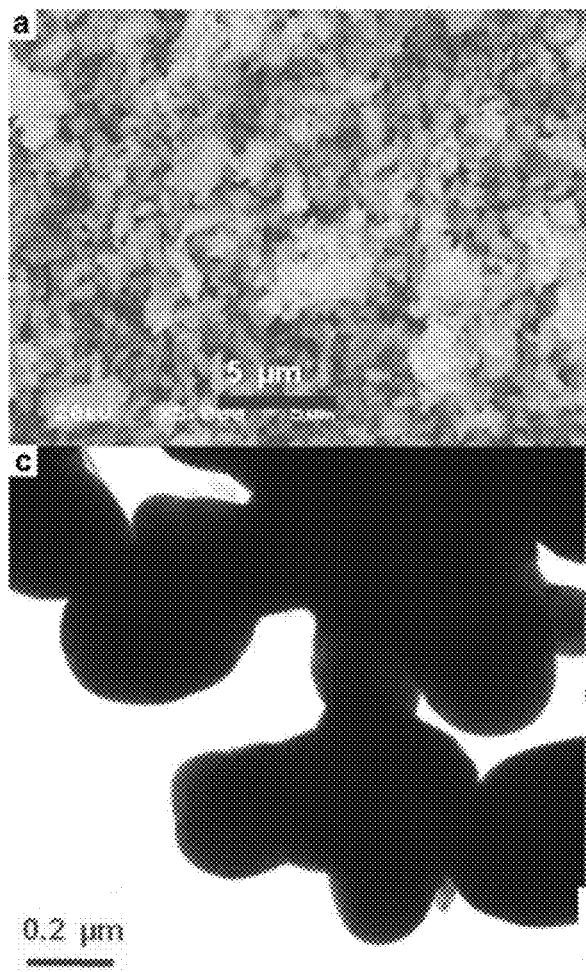
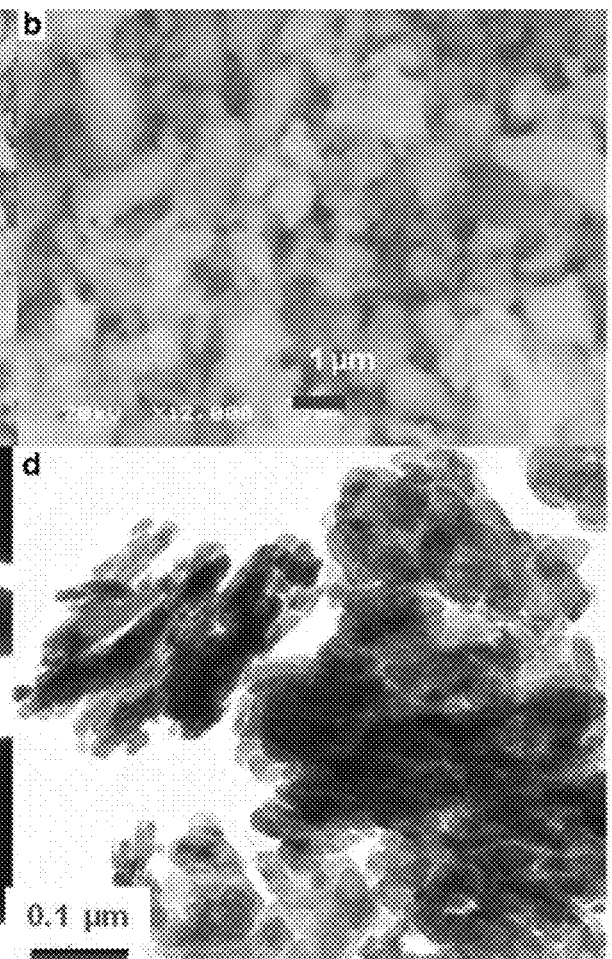
Figure 6c
Figure 6d

METHOD FOR TREATING AN AMMONIUM SALT

CROSS-REFERENCE TO RELATED APPLICATIONS

The present application is a Divisional of U.S. application Ser. No. 15/992,950, now allowed, having a filing date of May 30, 2018.

STATEMENT OF FUNDING ACKNOWLEDGEMENT

This project was funded by the Deanship of Scientific Research (DSR) at King Fahd University of Petroleum and Minerals (KFUPM) through Project No. SR161009.

BACKGROUND OF THE INVENTION

Field of the Disclosure

The present invention relates to a method of morphologically controlled synthesis of ferric oxide nano/microparticles.

Description of Related Art

Magnetic nano materials have many potential applications in various fields due to their well-regulated size and magnetic properties [Abu-Youssef et al. "Synthesis, structural characterization, magnetic behavior, and single crystal EPR spectra of three new one-dimensional manganese azido systems with FM, alternating FM-AF, and AF coupling" (1999) Inorg Chem 38:5716-5723]. Iron oxide magnetic nano spheres are either paramagnetic or super paramagnetic with a size fluctuating from a few nanometers to tens of nanometers. Iron oxide nanoparticles have attracted considerable attention from for investigators in a wide range of disciplines such as magnetic fluids [Caneschi et al. "Cobalt (II)-nitronyl nitroxide chains as molecular magnetic nanowires" (2001) Ang. Chem Int Ed 40:1760-1763], catalysis [Beswick et al. "Iron oxide nanoparticles supported on activated carbon fibers catalyze chemoselective reduction of nitroarenes under mild conditions" (2015) Catal Today 249:45-51], biotechnology-/biomedicine [Jain et al. "Iron oxide nanoparticles for sustained delivery of anticancer agents" (2005) Mol Pharm 2:194-205], magnetic resonance imaging [Babes et al. (1999) Synthesis of iron oxide nanoparticles used as MRI contrast agents: a parametric study. J Colloid Interf Sci 212:474-482], data storage [Rockenberger et al. "A new nonhydrolytic single-precursor approach to surfactant-capped nanocrystals of transition metal oxides" (1999) J Am Chem Soc 121:11595-11596] and environmental remediation [Baalousha et al. "Aggregation and surface properties of iron oxide nanoparticles: Influence of pH and natural organic matter" (2008) Environ Toxicol Chem 27:1875-1882]. Functionalized nanoparticles have found use as chemical catalyst [Obermayer et al. "Nanocatalysis in continuous flow: Supported iron oxide nanoparticles for the heterogeneous aerobic oxidation of benzyl alcohol" (2013) Green Chem 15:1530-1537], bio-label [Freitas et al. "Iron oxide/gold core/shell nanomagnetic probes and CdS biolabels for amplified electrochemical immunosensing of *Salmonella typhimurium*" (2014) Biosens Bioelectron 51:195-200], and bio-separation [Hola et al. "Tailored functionalization of iron oxide nanoparticles for MRI, drug delivery, magnetic separation and immobilization of biosubstances" (2015) Biotechnol Adv 33:1162-1176]. They are particularly useful as catalyst in liquid phase reactions because they are magnetically separable from the reaction medium, possess high catalytic activity, and are highly dispersible in solution [Camillo et al. "Hydrazine-mediated reduction of nitro and azide functionalities catalyzed by highly active and reusable magnetic iron oxide nanocrystals" (2013) J Org Chem 78:4530-4542; and Moghaddam et al. "Immobilized iron oxide nanoparticles as stable and reusable catalysts for hydrazine-mediated nitro reductions in continuous flow" (2014) ChemSusChem 7:3122-3131]. The magnetic moment of the nanoparticles directs the nanoparticles to the target biomolecule under physiological conditions.

Nanoparticles have different electrical, optical, magnetic, and chemical properties from those of the same material in bulk. It is well-known that the properties of nano materials are highly dependent on their morphology and structure. In particular, ferric oxide nano materials having different morphologies such as nanorods, [Mohapatra et al. "Iron oxide nanorods as high-performance magnetic resonance imaging contrast agents" (2015) Nanoscale 7:9174-9184; and Zhang et al. "Superior adsorption capacity of hierarchical iron oxide@ magnesium silicate magnetic nanorods for fast removal of organic pollutants from aqueous solution" (2013) Mater Chem A 1:11691-11697] nanotubes [Wu et al. "High responsivity photoconductors based on iron pyrite nanowires using sulfurization of anodized iron oxide nanotubes. (2014) Nano Lett 14:6002-6009] and nanospheres [Disch et al. "Quantitative spatial magnetization distribution in iron oxide nanocubes and nanospheres by polarized small-angle neutron scattering" (2012) New J Phys 14:013025; and Khosravi et al. "Adsorption of anionic dyes from aqueous solution by iron oxide nanospheres" (2014) J Ind Eng Chem 20:2561-2567] have gained considerable attention. Ferric oxide has found many applications in many fields because it is non-toxic, corrosion resistant, chemically stable, and environmentally friendly [Jamil et al. "Synthesis, characterization and catalytic application of polyhedron zinc oxide microparticles" (2017) Mater Res Exp 4:15902-15910]. Hydrothermal methods [Han et al. "One-step hydrothermal synthesis of 2D hexagonal nanoplates of $\alpha$-Fe2O3/graphene composites with enhanced photocatalytic activity" (2014) Adv Funct Mater 24:5719-5727], microwave hydrothermal [Li et al. "Microwave-assisted hydrothermal synthesis of $Fe_2O_3$-sensitized $SrTiO_3$ and its luminescent photocatalytic deNOx activity with $CaAl_2O_4$:(Eu, Nd) assistance" (2013) J Am Ceram Soc 96:1258-1262] and microwave solvothermal [Gutierrez et al. "A Microwave-assisted solvothermal synthesis of spinel $MV_2O_4$ (M=Mg, Mn, Fe, and Co)" (2014) Inorg Chem 53:8570-8576] are low temperature methods for the preparation of nanoscale materials of different sizes and shapes. Such methods save energy and are environmentally benign because reactions take place in closed and sealed containers. Synthesis of monodisperse nanometer-sized magnetic particles of metal alloys and metal oxides are currently an active area of investigation because they have potential wide range of applications including ultrahigh-density magnetic storage media and biological imaging. Size, size distribution, shape, and dimensionality determine the properties of the magnetic materials [Indira et al. "Magnetic nanoparticles-A review" (2010) Int J Pharm Sci Nanotechnol" 3:1035-1042; and Lu et al. "Magnetic nanoparticles: synthesis, protection, functionalization, and application" (2007) Angew Chem Int Ed 46:1222-1244]. Nanoparticles of various iron oxides ($Fe_3O_4$ and c-$Fe_2O_3$ in particular) have been widely used in wide range of applications. Iron oxide nanoparticles have been used as catalyst for thermal degradation of ammonium perchlorate (AP) and reduction of nitrophenols. Campos et al. ["Chemical and textural characterization of iron oxide nanoparticles and their effect on the thermal decomposition of ammonium perchlorate" (2015) Prop Expl Pyrotech 40:860-866] studied the thermal degradation of AP in the presence of $Fe_2O_3$ catalyst. Xu et al. ["Selective preparation of nanorods and micro-octahedrons of $Fe_2O_3$ and their catalytic performances for thermal decomposition of ammonium perchlorate" (2008) Powder Technol 185:176-180] used $Fe_2O_3$ microoctahedrons and nanorods as catalyst for thermal degradation of AP. Alizadeh-Gheshlaghi et al. ["Investigation of the catalytic activity of nano-sized CuO, $Co_3O_4$ and $CuCo_2O_4$ powders on thermal decomposition of ammonium perchlorate" (2012) Powder Technol 217:330-339] compared the catalytic activities of copper oxide, copper chromite and cobalt oxide nanoparticles. They found that copper chromite has the highest catalytic activity in the thermal decomposition reaction of AP. While the effect of size of the nanoparticle have been examined in details, the effects solvent on size and morphology of magnetite ($Fe_3O_4$) particles and their catalytic properties is much less understood.

Accordingly, it is the object of the present disclosure to provide a solvothermal method of controlling the morphology of magnetite ($Fe_3O_4$) micro and nanoparticles at low temperature without the use of any templating agent. Also, the disclosure describes the effect of morphology and size of particles on their catalytic properties in the thermal decomposition of ammonium perchlorate and the reduction of nitro compounds by sodium borohydride to the corresponding amines in aqueous medium.

SUMMARY

A first aspect of the invention is directed to a method of forming ferric oxide nano/micro particles comprising:
  heating a composition comprising a ferric halide and an alkali metal salt of a carboxylic acid in a solvent at a temperature of 150-300° C. in a sealed container to form the ferric oxide nano/micro particles,
  wherein the ferric oxide nano/micro particles formed by the heating have a predominant morphology, and
  wherein the solvent is not ethylene glycol or polyethylene glycol.

In a preferred embodiment, the predominant morphology is selected from the group consisting of a porous hollow sphere, a microsphere, a micro rectangular plate, and an octahedron.

In another preferred embodiment, the ferric halide is ferric chloride.

In another preferred embodiment, the alkali metal salt of a carboxylic acid is sodium acetate.

In another preferred embodiment, the solvent is at least one selected from the group consisting of water, methanol, ethanol, propanol, isopropanol, butanol, isobutanol, t-butanol, acetonitrile, acetone, dimethylformamide (DMF), tetrahydrofurane, and dimethyl sulfoxide (DMSO).

In another preferred embodiment, the solvent is at least one selected from the group consisting of ethyl acetate, diethyl ether, pentane, isopentane, cyclopentane, n-hexane, cyclohexane, heptane, benzene, toluene, o-xylene, m-xylene, and p-xylene.

In another preferred embodiment, the solvent comprises at least one solvent selected from the group consisting of methanol, ethanol, propanol, isopropanol, butanol, isobutanol, t-butanol, acetonitrile, acetone, DMF, tetrahydrofurane, and DMSO and at least one other solvent selected from the group consisting of ethyl acetate, diethyl ether, pentane, isopentane, cyclopentane, n-hexane, cyclohexane, heptane, benzene, toluene, o-xylene, m-xylene, and p-xylene.

In another preferred embodiment, the solvent comprises at least one first solvent selected from the group consisting of ethylene glycol and polyethylene glycol, and at least one second solvent selected from the group consisting of water, methanol, ethanol, propanol, isopropanol, butanol, isobutanol, t-butanol, acetonitrile, acetone, DMF, tetrahydrofurane, DMSO, ethyl acetate, diethyl ether, pentane, isopentane, cyclopentane, n-hexane, cyclohexane, heptane, benzene, toluene, o-xylene, m-xylene, and p-xylene.

In a more preferred embodiment, the solvent is combination of at least two solvents selected from the group consisting of water, ethylene glycol, polyethylene glycol, and n-hexane.

In another preferred embodiment, the heating temperature is in the range of about 195 to 205° C.

In another preferred embodiment, the predominant morphology of the ferric oxide nano/microparticle is selected from the group consisting of porous hollow sphere, microsphere, micro rectangular plate, octahedral, and irregular shape.

In another preferred embodiment, the particle diameter of the nano/microparticles is in the range of about 20 nm to about 25 μm.

A second aspect of the invention is directed to a ferric oxide nano/micro particles having a predominant morphology produced by the method described herein.

In a preferred embodiment, the predominant morphology of the ferric oxide nano/microparticles is selected from the group consisting of porous hollow sphere, microsphere, micro rectangular plate, octahedral, and irregular shape.

In another preferred embodiment, the particle diameter of the ferric oxide nano/microparticles is in the range of about 20 nm to about 25.0 μm.

A third aspect of the invention is directed to a method of catalyzing a reduction of a nitro compound to an amine compound, said method comprising:
  contacting a solution comprising the nitro compound and sodium borohydride with a ferric oxide nano/micro particles with predominant morphology.

In a preferred embodiment, the ferric oxide nano/micro particles have a predominant morphology selected from the group consisting of a hollow sphere, a microsphere, a micro rectangular plate, and an octahedron.

A fourth aspect of the invention is directed to a method of catalyzing the decomposition of an ammonium salt, said method comprising contacting the ammonium salt with a ferric oxide nano/micro particles with predominant morphology.

In a preferred embodiment, the ferric oxide nano/micro particles have a predominant morphology selected from the group consisting of a hollow sphere, a microsphere, a micro rectangular plate, and an octahedron.

In another preferred embodiment of the method, the method further comprises heating the mixture to a temperature in the range of 250 to 450° C.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2a shows SEM image of Fe₃O₄ product A.

FIG. 2b shows TEM image of product A.

FIG. 2c shows hollow spherical aggregates of product A.

FIG. 2d shows spherical aggregate of product A.

FIG. 2e shows an HRTEM image of product A.

FIG. 2f shows an HRTEM image of product A.

FIG. 5a shows SEM overview product D.

FIG. 5b shows octahedral particles of product D aggregated together in the form of cylindrical rod.

FIG. 5c shows several octahedral particles of product D.

FIG. 5d shows a single octahedral particle of product D.

FIG. 6a shows the SEM images of product E.

FIG. 6b shows the SEM images of product E.

FIG. 6c shows TEM images of product E.

FIG. 6d shows TEM images of product E.

DETAILED DESCRIPTION

Figure 1:
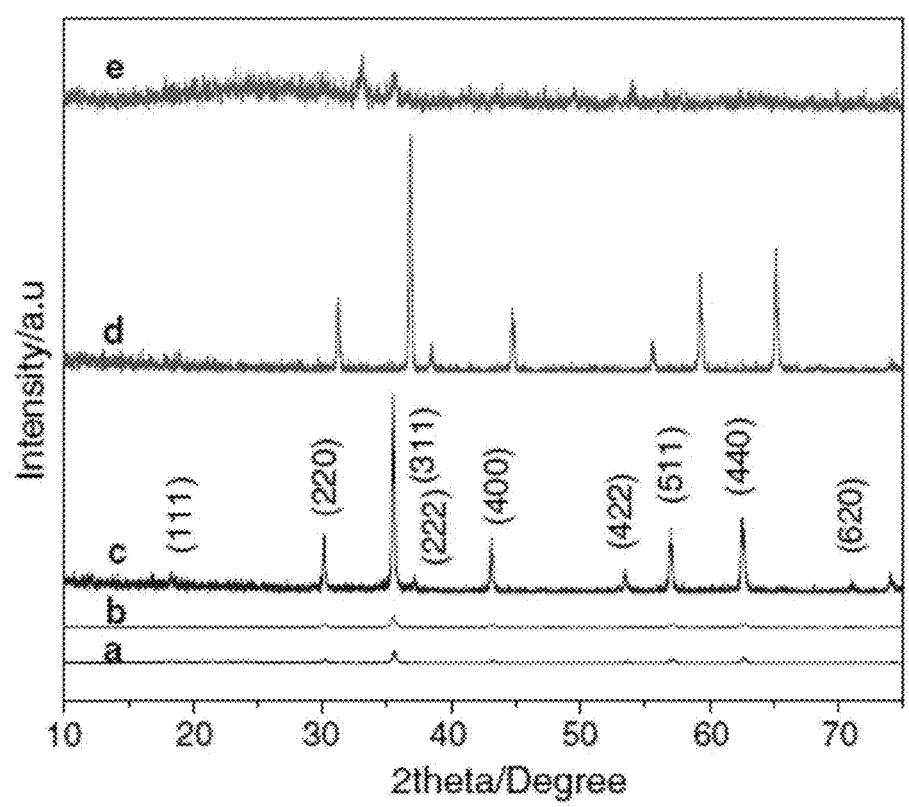
FIG. 1 shows XRD patterns of Fe₃O₄. XRD patterns a-e correspond to product A-E, respectively.

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

As used herein, the term "compound" is intended to refer to a chemical entity, whether in a solid, liquid or gaseous phase, and whether in a crude mixture or purified and isolated.

As used herein, the term "salt" refers to derivatives of the disclosed compounds, monomers or polymers wherein the parent compound is modified by making acid or base salts thereof. Exemplary salts include, but are not limited to, mineral or organic acid salts of basic groups such as amines, and alkali or organic salts of acidic groups such as carboxylic acids. The salts of the present disclosure can be synthesized from the parent compound that contains a basic or acidic moiety by conventional chemical methods. Generally such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, ±0.4, ±0.3, ±0.2, or ±0.1.

As used herein, the term "alkyl" unless otherwise specified refers to both branched and straight chain saturated aliphatic primary, secondary, and/or tertiary hydrocarbons of typically $C_1$ to $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. As used herein, the term optionally includes substituted alkyl groups. Exemplary moieties with which the alkyl group can be substituted may be selected from the group including, but not limited to, hydroxyl, alkoxy, aryloxy, or combination thereof.

As used herein, the term "substituted" refers to at least one hydrogen atom that is replaced with a non-hydrogen group, provided that normal valences are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylation, arylthio, arylalkylthio, alkylthiono, arylthiono, aryalkylthiono, alkylsulfonyl, arylsulfonyl, arylalkylsulfonyl, sulfonamide (e.g. —$SO_2NH_2$), substituted sulfonamide, nitro, cyano, carboxy, carbamyl (e.g. —$CONH_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

As used herein, the term "aryl" unless otherwise specified refers to functional groups or substituents derived from an aromatic ring including, but not limited to, phenyl, biphenyl, naphthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

As used herein, the term "alcohol" unless otherwise specified refers to a chemical compound having an alkyl group bonded to a hydroxyl group. Many alcohols are known in the art including, but not limited to, methanol, ethanol, propanol, isopropanol, butanol, isobutanol and t-butanol, as well as pentanol, hexanol, heptanol and isomers thereof. Since the alkyl group may be substituted with one or more hydroxyl group, the term "alcohol" includes diols, triol, and sugar alcohols such as, but not limited to, ethylene glycol, propylene glycol, glycerol, and polyol.

As used herein, the term "template" refers to as a structure directing agent and is stable under hydrothermal aging conditions and furthermore hydrophobic relative to the metal salts. Many templates used in the manufacturing nanoparticles are known in the art. They include all types of surfactants including anionic surfactants, cationic surfactants, and neutral surfactants. The surfactant may act as a nucleation site for the formation of the nanoparticles. Alkyl ammonium salts are commonly used as templates to form structures in solution that interacts with the inorganic material in solution and serve as a template for the growth of nanoparticles. A commonly used template is tetrapropylammonium hydroxide, tetraethylammonium hydroxide, tetrabutylammonium hydroxide, or tetrapentylammonium hydroxide. Other known templates include cetyl trimethylammonium bromide, cetyl triethylammonium bromide, or dodecyl triethylammonium bromide. Other known templating agents are polymers such as Pluronic F127, Pluronic P123, Brij-56, or Brij-30. The template is usually decomposed during calcining at temperatures in the range 545-600° C. for 6-10 hours.

As used herein the term "predominant morphology" refers to a morphology that is present in a major amount or an amount that is significantly more than any other morphology or combination of morphologies in a preparation of nano/microparticles of ferric oxide as observed in SEM and/or TEM images. In the instant disclosure, several predominant morphologies have been observed by SEM and/or TEM including the porous hollow sphere, microsphere, microrectangular platelet, octahedron, and irregular shape shown in FIGS. 2-6, respectively.

The present disclosure is further intended to include all isotopes of atoms occurring in the present compounds. Isotopes include those atoms having the same atomic number but different mass numbers. By way of general example, and without limitation, isotopes of oxygen include $^{16}O$, $^{17}O$, and $^{18}O$. Isotopes of iron include $^{54}Fe$, $^{56}Fe$, $^{57}Fe$ and $^{58}Fe$. Isotopically labeled compounds of the invention can generally be prepared by conventional techniques known to those skilled in the art or by processes and methods analogous to those described herein, using an appropriate isotopically labeled reagent in place of the non-labeled reagent otherwise employed.

A first aspect of the invention is directed to method of forming ferric oxide nano/micro particles comprising:
    heating a composition comprising ferric halide and alkali metal salt of a carboxylic acid in a solvent at a temperature of 150-300° C. in a sealed container to form a ferric oxide nano/micro particles,
    wherein the ferric oxide nano/micro particles formed by the heating have a predominant morphology, and wherein the solvent is not ethylene glycol or a mixture of polyethylene glycol and ethylene glycol.

The method is a solvothermal method for preparing ferric oxide nano/microparticle having predominant morphologies using different solvents or combinations of solvent. Thermal treatment of a reaction mixture comprising ferric halide and alkali metal salt of a carboxylic acid in different solvents produces different predominant morphologies. The solvent may be a polar solvent, a non-polar solvent or a combination thereof.

In a preferred embodiment, the solvent is a polar solvent. The polar solvent can be protic or aprotic polar solvent. Protic solvents include, but not limited to water or mono-, di-, and trihydroxy compound. Monohydroxy compounds include alcohols such as, but not limited to, methanol, ethanol, propanol, isopropanol, butanol, isobutanol, t-butanol, pentanol, cyclopentanol, cyclohexanol, phenol, hexanol, cycloheptanol, heptanol, cyclooctanol, octanol, phenol, or isomers thereof. Dihydroxy compounds include ethylene glycol, propylene glycol, butylene glycol, and oligomer and polymers thereof are particularly preferred solvents for the method. Also, trihydroxy compounds such as glycerol may be used in the method alone or in combination with any other solvent. In a more preferred embodiment, the solvent is water, methanol, ethanol, propanol, isopropanol, butanol, isobutanol, t-butanol, ethylene glycol, propylene glycol, butylene glycol, or combinations thereof.

In another preferred embodiment, the solvent is a polar aprotic solvent including, but not limited to, acetonitrile, acetone, tetrahydrofuran (THF), dimethylformamide (DMF), dimethyl sulfoxide (DMSO), or combinations thereof.

In another preferred embodiment, the solvent is a non-polar solvent such as a halogenated hydrocarbon including, but not limited to chloromethane, dichloromethane, chloroform, tetrachloromethane, chloroethane, and dichloroethane. Other non-polar solvents include, but are not limited to, diethyl ether, methylethylether, diethylether, pentane, ethyl acetate, isopentane, cyclopentane, n-hexane, cyclohexane, n-heptane, benzene, toluene, o-, m-, or p-xylene, and combination thereof.

In another preferred embodiment, the solvent is a mixture of polar solvents and non-polar solvents. The mixture may contains polar solvent in the range of 5% to 95%, preferably in the range of 20% to 80%, more preferably in the range of 30% to 70%, and even more preferably in the range of 40% to 60%, and most preferably in the range of 45% to 55%.

In a more preferred embodiment, the solvent is a mixture of water and ethylene glycol or polyethylene glycol, preferably the mixture contains water in the range of 10% to 90%, more preferably in the range of 30% to 70%, and most preferably in the range of 45% to 55%.

In another preferred embodiment, the solvent is a mixture of non-polar solvent and ethylene glycol or polyethylene glycol. In a more preferred embodiment, the solvent is a mixture of n-hexane and ethylene glycol or polyethylene glycol, preferably the mixture contains n-hexane in the range of 10% to 90%, more preferably in the range of 30% to 70%, and most preferably in the range of 45% to 55%. In a particular preferred embodiment the mixture contains 50% water in ethylene glycol or polyethylene glycol.

Any ferric halide may be used in the method including ferric fluoride, ferric chloride, ferric bromide, or ferric iodide. In a preferred embodiment, the ferric halide is ferric chloride.

Similarly, any alkali metal salt of a carboxylic acid may be used in the method. In a preferred embodiment, the alkali metal salt includes, but is not limited to, one or more of lithium, sodium, or potassium salt. The salt may be any carboxylic acid salt such as, but not limited to, formic acid, acetic acid, propionic acid, butyric acid, citric acid, oxalic acid, or tartaric acid. In a particularly preferred embodiment, the alkali metal salt of a carboxylic acid is sodium acetate.

The method may produce nano/microparticle having any morphology. In a preferred embodiment, the morphology of the particle is selected from the group consisting of a porous hollow sphere, a microsphere, a micro rectangular plate, and an octahedron.

The method includes heating a composition of ferric halide and alkali metal salt in a solvent at a temperature, preferably substantially constant, for a time in the range of 8 to 36 hours, preferably in the range of 10 to 32 hours, more preferably in the range 12 to 24 hours, and most preferably in the range of 16 to 20 hours. In a particular preferred embodiment, the time of heating is 18 hours. The heating temperature is in the range of 150 to 300° C., preferably in the range of 170 to 250° C., more preferably in the range of 190 to 230° C., and most preferably in the range of about 195 to 205° C. The method disclosed herein has several advantages. One advantage of the method is that there is no need or requirement for a templating agent such as tetrapropylammonium hydroxide, tetraethylammonium hydroxide, tetrabutylammonium hydroxide, or tetrapentylammonium hydroxide. Other known templates include cetyl trimethylammonium bromide, cetyl triethylammonium bromide, dodecyl triethylammonium bromide, Pluronic F127, Pluronic P123, Brij-56, or Brij-30 to obtain the various morphologies of $Fe_3O_4$. Finally, the solvothermal method is carried out at relatively low temperature. Various morphologies of the nano/microparticles of $Fe_3O_4$ can be obtained by varying the solvent and its composition.

In some embodiment, the ferric oxide nano/microparticle has any geometrical shape such as, but not limited to, a porous hollow sphere, a sphere, a micro rectangular plate, octahedral, or irregular shape.

Similarly, the diameter of the ferric oxide nano/microparticle may vary in the range of 10 nm to about 50 μm depending on the reaction conditions, in particular, the solvent composition. In some embodiments, the particle diameter is in the range of about 10 nm to about 25.0 μm, more preferably in the range of about 20 nm to about 15 μm, and most preferably in the range of about 100 nm to about 5 μm.

A second aspect of the invention is directed to ferric oxide nano/micro particles with predominant morphology produced by the method described herein.

In a preferred embodiment, the morphology of the ferric oxide nano/microparticle is selected from the group consisting of porous hollow sphere, microsphere, micro rectangular plate, octahedral, and irregular shape.

A third aspect of the invention is directed to a method of catalyzing a reduction reaction of a nitro compound to the corresponding amine, said method comprising:
  contacting a solution comprising the nitro compound and sodium borohydride with ferric oxide nano/micro particles which have a predominant morphology selected from the group consisting of a hollow sphere, a microsphere, a micro rectangular plate, and an octahedron.

The nitro compound may be any nitro compound such as alkyl or aryl nitro compound to produce the corresponding amine. Many aliphatic and aromatic nitro compounds are known in the art and may be utilized in the method including, but not limited to nitro methane, nitroethane, nitroglycerine, nitrobenzene, dinitrobenzene, trinitrobenzene, nitrotoluene, dinitrotoluene, trinitrotoluene, nitrophenol, dinitrophenol, and trinitrophenol, also known as picric acid.

The method comprises contacting the nitro compound with a reducing agent in the presence of the ferric oxide nano/microparticle with a predominant morphology in a solvent. The reducing agent may be any reducing agent which is capable of reducing a nitro compound to the corresponding amine. Several reducing agents are well-known in the art including, but not limited to hydrogen gas or sodium borohydride. The solvent may be any solvent in which the nitro compound is soluble and may be polar solvent, apolar solvent or mixture thereof. The polar solvent may be protic solvent such as, but not limited to, water and alcohols such as methanol, ethanol, propanol, isopropanol, butanol, isobutanol, t-butanol, and the like. Also, the polar solvent may be polar aprotic solvent such as, but not limited to acetone, acetonitrile, dimethylformamide, tetrahydrofurane, dioxane, and the like. In some embodiments of the method, apolar solvent such as hexane, diethyl ether, chloroform, methylene chloride, tetrachlormethane, and the like solvent may be used.

In a preferred embodiment of the method the reaction mixture may be heated to accelerate the reaction, whereas in some other embodiment the reaction may be cooled to dissipate the heat produced by the reaction.

In a particularly, preferred embodiment, the method is carried out in aqueous solution at ambient temperature. The solution may be buffered to maintain constant pH of the reaction solution. Many buffers are known in the art depending on the desired pH of the reaction including, but not limited to, acetate, carbonate buffers, phosphate buffers, Tris, Mops, HEPES, and the like.

A forth aspect of the invention is directed to a method of catalyzing the decomposition an ammonium salt, said method comprising contacting the ammonium salt with nano/micro particles described herein. The ammonium salt of the method can be any ammonium salt including that of ammonia, alkyl amines, and aryl amines. Any salt of ammonia such as, but not limited to, ammonium fluoride, ammonium chloride, ammonium bromide, ammonium iodide, ammonium nitrate, ammonium acetate, ammonium oxalate and the like. Other ammonia derivatives such as but not limited to hydrazine and its alkyl and aryl derivatives may be used in the method. Also, the method may utilize ammonium salts of primary, secondary, or tertiary amines as well as aryl amines. Examples of such ammonium salts include but not limited to methylammonium chloride, methyl ammonium bromide, ethyl ammonium chloride, isopropylammonium chloride, aniline hydrochloride, o-, m-, or p-diaminobenzene hydrochloride, and o-, in-, or p-toluidine hydrochloride. The method comprises mixing the ammonium salt with nano/microparticles and heating the mixture.

In a preferred embodiment of the method, the nano/microparticles have a predominant morphology selected from the group consisting of a hollow sphere, a microsphere, a micro rectangular plate, and an octahedron. Since the method is carried out with solid material, the method may include step to homogenize the solid material which may include grinding, mechanical mixing, and/or sonication.

The decomposition reaction may be heated at a temperature in the range of 200 to 500° C., preferably in the range of 250 to 450° C. and more preferably in the range of 300 to 400° C.

The examples below are intended to further illustrate protocols for the preparation and characteristics of the ferric oxide nano-/microparticles described above, and are not intended to limit the scope of the claims.

Example 1

Materials and Methods:
Materials: All the chemicals are purchased commercially and used without any further purification. Ferric chloride (FeCl3·6H2O), sodium borohydride (NaBH4), sodium ethanoate, polyethylene glycol-200, n-hexane, absolute alcohol (e.g., ethanol), ammonium perchlorate (AP), 4-nitrophenol (4-NP), and ethylene glycol (EG) are utilized for the synthesis of nano/micro particles. Deionized water is used throughout the experimental work.
Methods:
Catalytic Activities:
(a) Thermal decomposition of ammonium perchlorate-catalyzed by the ferric oxide nano/microparticles is studied in a mixture 1% (w/w) of catalyst in AP. In a typical experiment, 0.1 g of catalyst and 9.9 g of AP were mixed and grounded to ensure homogeneity, and the reaction was monitored by NEZSCH TGA thermogravimetric analyzer.

(b) The reduction of 4-NP by $NaBH_4$-catalyzed by the ferric oxide nano/microparticles. In a typical measurement, 1.8 mL of 0.111 mM 4-NP in water, 0.5 mL of 50 mM in water, and 1.0 μg $Fe_3O_4$ catalyst were added in a cuvette. Time dependent UV-Vis spectra were recorded between 200-500 nm every 5 minutes on UVD3500 spectrophotometer until no further changes at wave length 300 and 400 nm were observed (see FIG. 9a).

Structural Characterization: X-ray powder diffraction (XRD) patterns were obtained on a Rigaku D/max Ultima III X-ray diffractometer with a Cu-Kα radiation source (λ=0.15406 nm) operated at 40 kV and 150 mA at a scanning step of 0.02° in range of 2θ of 10-80°. Scanning electron microscopy observation was performed on a JEOL JSM-6480A scanning electron microscope. Transmission electron microscopy (TEM) observation was performed on an FEI Tecnai G2 S-Twin TEM with an accelerating voltage of 200 kV. Thermogravimetric measurements were carried out on NEZSCH STA 409 PC with a heating rate of 10° C./min from 50 to 600° C. UVD3500, Shimadzu was used to monitor the catalytic reduction of 4-NP.

Example 2

Synthesis of ferric oxide nano/micro particles: A 30 mL solution of 1.35 g of $FeCl_3·6H_2O$ in ethylene glycol is added to a 30 mL solution of 3.6 g of sodium acetate in ethylene glycol and stirred for 30 minutes. The resulting black liquid was transferred to Teflon lined autoclave of 100 mL capacity. The autoclave was sealed at a constant temperature of 200° C. for 18 h. After heating, the autoclave is allowed to cool to room temperature, and the product was collected by centrifugation at 3000 rpm. The resulting product was washed three times with deionized water and three times with absolute alcohol. The washed precipitates were dried in a vacuum oven at 60° C. for 12 h to produce product A. The same protocol is used to obtain product B except that the ethylene glycol solvent is replaced with 50% aqueous ethylene glycol. Similarly, product C, D, and E are produced by the same method using polyethylene glycol, n-hexane, and 50% ethylene glycol in n-hexane, respectively. Table 1 summarizes the solvent composition for products A-E.

TABLE 1

Comparison of effect of nature and composition of solvent on morphology and diameter of Fe3O4 particles and their catalytic properties

| | Solvent Composition | Particles Morphology | Diameter | Catalytic thermal decomposition of AP | | | Catalytic Reduction of 4-NP $K_{app}$ min$^{-1}$ |
|---|---|---|---|---|---|---|---|
| | | | | Final DT$^a$ °C. | Temp.$^b$ °C. | Red. Of final decomp. Temp. °C. | |
| A | Ethylene glycol | Porous hollow sphere | 140 nm | 310 | 285 | 140 | 0.4206 |
| B | 50% aqueous ethylene glycol | Microsphere | 415 nm | 345 | 329 | 105 | 0.3073 |

TABLE 1-continued

Comparison of effect of nature and composition of solvent on morphology
and diameter of Fe3O4 particles and their catalytic properties

| | Solvent Composition | Particles Morphology | Diameter | Final DT[a] °C. | Temp.[b] °C. | Red. Of final decomp. Temp. °C. | Catalytic Reduction of 4-NP $K_{app}$ min$^{-1}$ |
|---|---|---|---|---|---|---|---|
| | | | | Catalytic thermal decomposition of AP | | | |
| C | Polyethylene glycol | Microrectangular platelet | ~12 μm | 390 | 373 | 60 | 0.3054 |
| D | n-Hexane | Octahedron | ~4.3 μm | 420 | 387 | 30 | 0.2834 |
| E | 50% n-hexane in ethylene glycol | Irregular | ~4 μm | 400 | 360 | 50 | 0.2837 |

[a]Decomposition Temperature.
[b]Temperature of maximum loss in mass percentage.

Example 3

Structural Characterization:
XRD Analysis

XRD patterns of products are shown in FIG. 1. XRD data analysis shows that product is $Fe_3O_4$. The position and relative intensity of all diffraction lines match well with those of the commercial magnetite powder (Aldrich catalog No. 31,006-9) reported by Sun et al. [Sun et al. "Size-controlled synthesis of magnetite nanoparticles." (2002) J Am Chem Soc 124:8204-8205]. The results of XRD data analysis for products A-D are summarized in Table 2. Diffraction lines analysis of FIGS. 1a and 1b indicate that product A and B possess monoclinic unit cell structure. In contrast, the results of FIGS. 1c and 1d indicate that product C and D possess face centered cubic unit cell structure. Similarly, Lin et al. and Mckenna et al. have shown that $Fe_3O_4$ is crystallized in cubic unit cells [Lin et al. "Encapsulated $Fe_3O_4$/Ag complexed cores in hollow gold nanoshells for enhanced theranostic magnetic resonance imaging and photothermal therapy. (2014) Small 10:3246-3251; and McKenna et al. "Atomic-scale structure and properties of highly stable antiphase boundary defects in $Fe_3O_4$." (2014) Nat Commun 5:9-10]. Wright et al. ["Charge ordered structure of magnetite $Fe_3O_4$ below the Verwey transition. (2002) Phys Rev B 66:214422] has determined that $Fe_3O_4$ is crystallized in a monoclinic unit cells. The absence of any extraneous peaks in the XRD patterns indicates that the products are highly pure. The well-defined sharp diffraction lines confirmed that products are highly crystalline.

SEM and SEM Observation

Table 1 summarizes the morphology and diameter of the products, the solvent composition used in their synthesis, and their catalytic properties.

Product A: Porous Hollow Spheres of $Fe_3O_4$.

SEM and TEM images of product A are shown in FIG. 2. FIG. 2a shows an overview of the product indicating that the particles diameter is small and formed aggregates. Thus, the morphology of the product and estimate of the average diameter of particles could not be determined by SEM. TEM micrographs of product A are shown in FIGS. 2b-d indicating that product A is nearly spherical in shape. The particle diameter is small about 10 nm and assembled into large spheres. The large spheres are not uniform in diameter with some irregularity. The spherical aggregates of nanoparticles appear to be hollow. Also, FIG. 2c confirms the presence of hollow spheres with a wide opening at the apical surface indicated by red arrow in the FIG. 2c. The product $Fe_3O_4$ is formed by loosely packed nanoparticles leading to small pores (see FIG. 2d). The average diameter of these hollow spheres is approximately 140 nm. Some of the spherical aggregates are visible in microscopic images and probably are fragmented from the large spheres.

Figure 2G:
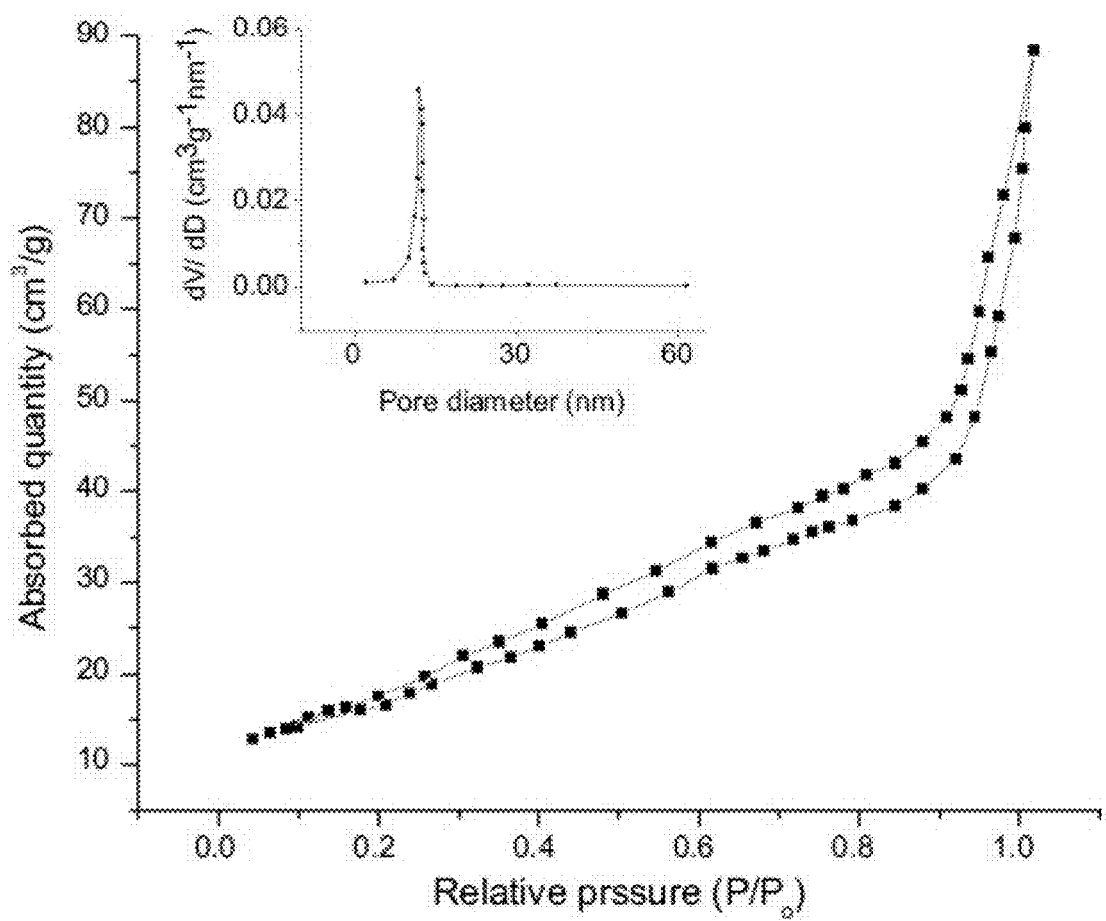
FIG. 2g shows nitrogen adsorption-desorption isotherm and corresponding BJH pore-diameter distribution curve of product A.

HRTEM images of the $Fe_3O_4$ microspheres and nanospheres obtained are shown in FIGS. 2e and 2f. It can be seen that the nanoparticles well-organized and assembled into a single crystal, even though some open pores and defects are visible in HRTEM images. There are clear boundaries of the assembled small $Fe_3O_4$ nanoparticles. The particles of product A are hollow which is confirmed by SEM and TEM observations. The result presented here shows that the use of ethylene glycol solvent in the solvothermal method produced a uniform spherical morphology. The hollow sphere and porous structure may have been resulted from carbon dioxide or methane gas trapped inside the spheres. As the temperature rises in the solvothermal method, the trapped gas pressure in the spheres increases and form a gas bubble leading to increase the diameter of spheres. At certain point, the bubble is burst and the gas escape leaving an opening and on the pores surfaces. Also, the porosity of product A is examined by nitrogen adsorption desorption isotherm shown in FIG. 2g. The results indicate that product A is porous with calculated specific surface area of 35.63 m$^2$/g.

Product B: Microsphere of $Fe_3O_4$.

Figures 3A, 3B, 3C, 3D, 3E, 3F:
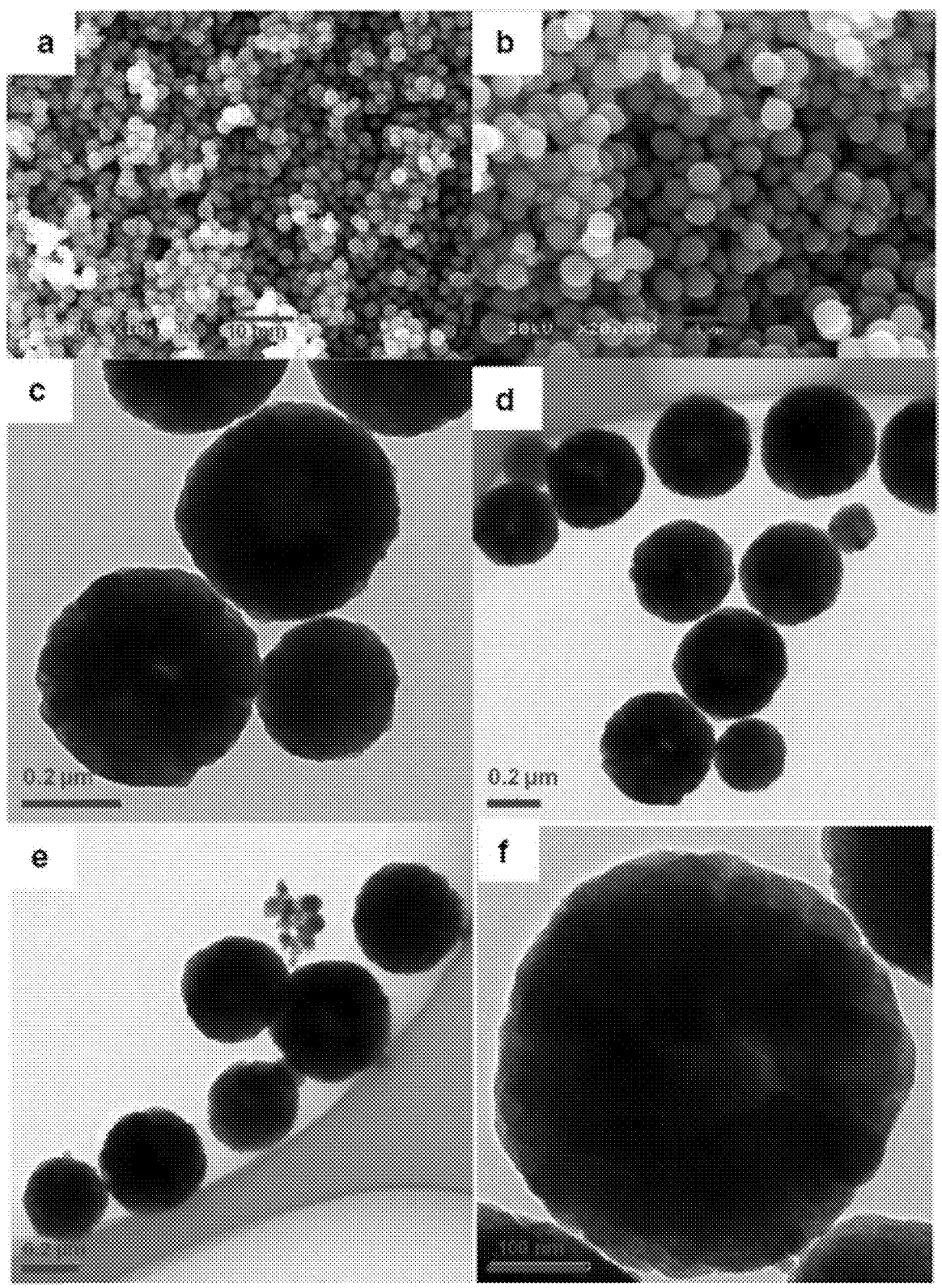
FIG. 3a shows SEM overviews of the microspheres of product B.
FIG. 3b shows SEM overviews of the microspheres of product B.
FIG. 3c shows SEM overviews of the microspheres of product B.
FIG. 3d shows TEM overview of microspheres of product B.
FIG. 3e shows TEM overview of microspheres of product B.
FIG. 3f shows TEM of a single microsphere of product B.
Figure 3G:
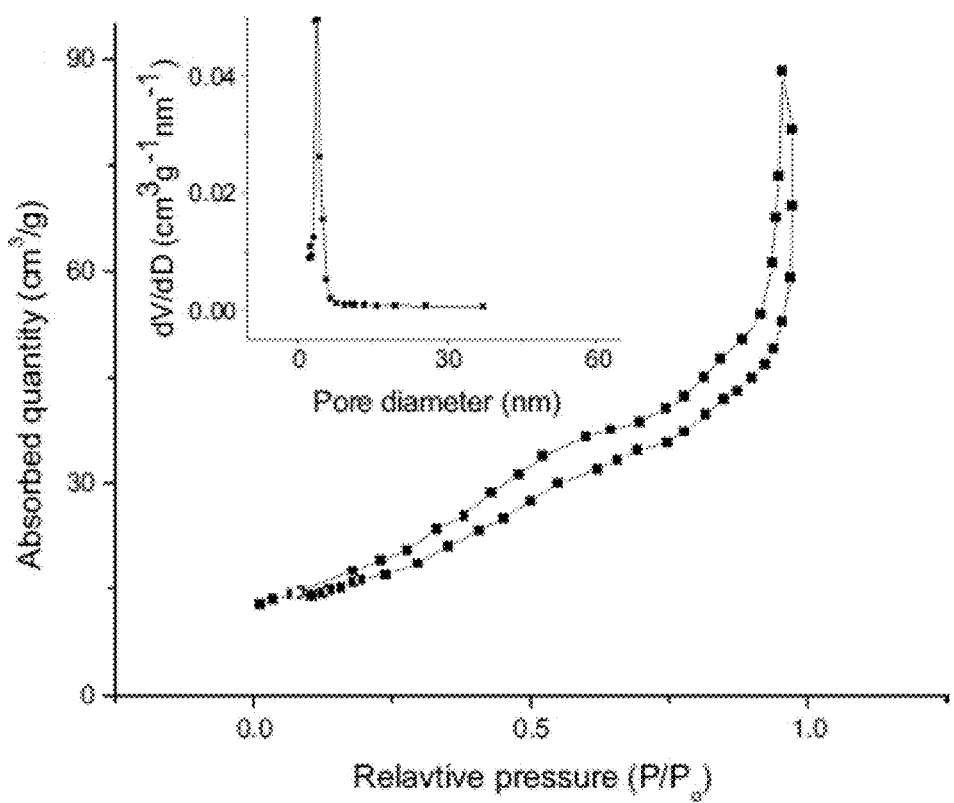
FIG. 3g shows nitrogen adsorption-desorption isotherm and the corresponding BJH pore-diameter distribution curve (inset) of product B.

Product B is obtained by using 50% ethylene glycol in deionized water as solvent. Product B has been characterized by SEM and TEM and the results are shown in FIG. 3. The SEM observation shows that the product is fairly spherical with no opening. The diameter of these particles varied in the range of 140-415 nm and most particles are about 415 nm. The product appeared as bulk and clustered together due to very large amount of spherical particles present among the product B, see FIGS. 3a-3c.

TEM observations, shown in FIG. 3d-3f, are in good agreement with the results obtained by SEM images. Product B is uniformly spherical with distinct boundaries and compact shape without any irregularities in the morphology. The average diameter of the product measured by TEM micrograph is approximately 415 nm, and a few nanospheres are also observed along with these nanoparticles.

The edges of these microparticles are very sharp with no zigzag confirming that the product B is uniformly spherical in shape. The TEM images show the contrast of light and dark colors that either confined to the presence of very thin walls/boundaries of the nanoparticles or indicating the presence of cavity inside the spheres. These spheres may be hollow but no broken microsphere has been observed in SEM and TEM micrographs. Nitrogen adsorption-desorption isotherm is used for analysis of porosity of product B, see FIG. 3g. The isotherm shows that product B is porous and BET pore diameter distribution is calculated at 22.9 m²/g.

Product C. Micro Rectangular Platelets of $Fe_3O_4$.

Figures 4A, 4B, 4C, 4D:
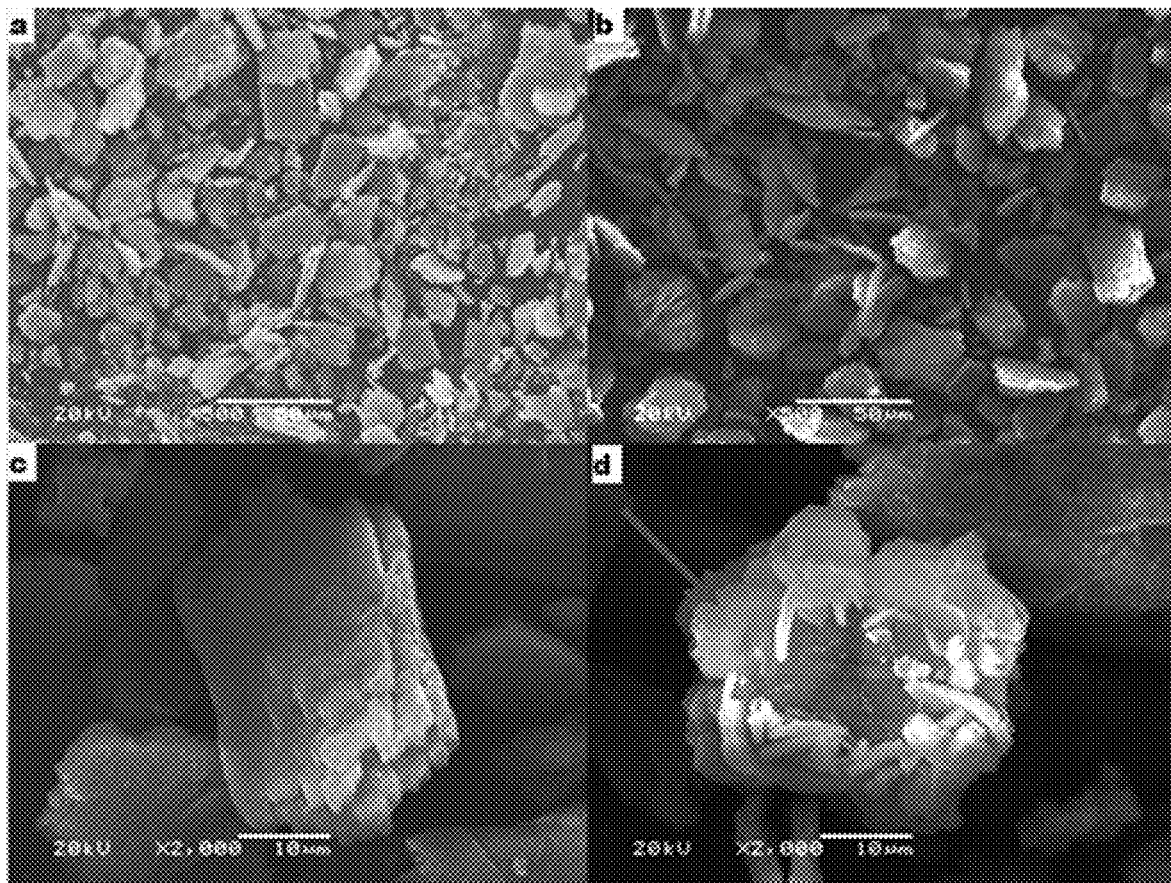
FIG. 4a shows SEM overviews of product C of micro rectangular platelets of Fe₃O₄.
FIG. 4b shows SEM overviews of product C of micro rectangular platelets of Fe₃O₄.
FIG. 4c shows SEM view of the micro rectangular platelets of Fe₃O₄ of product C.
FIG. 4d shows the flower-like structure formed by discs of product C.
Figure 7A:
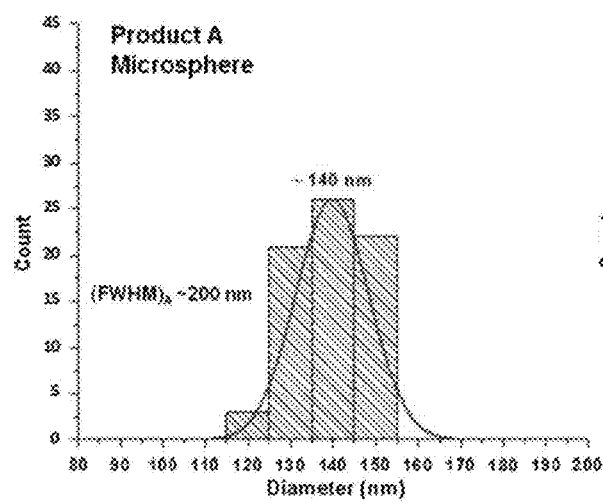
FIG. 7A shows the diameter distribution histograms of products A.
Figure 7B:
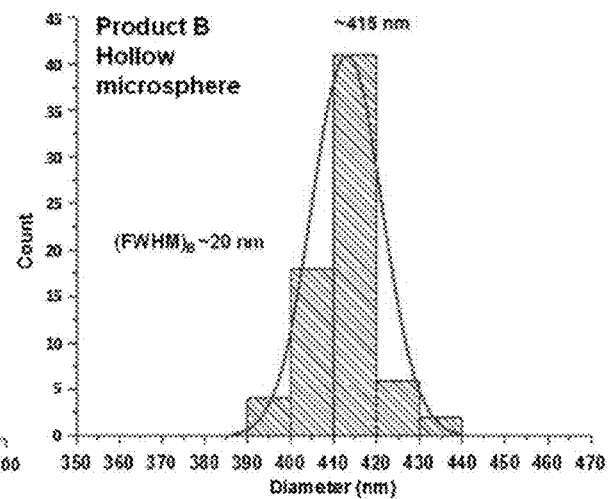
FIG. 7B shows the diameter distribution histograms of products B.
Figure 7C:
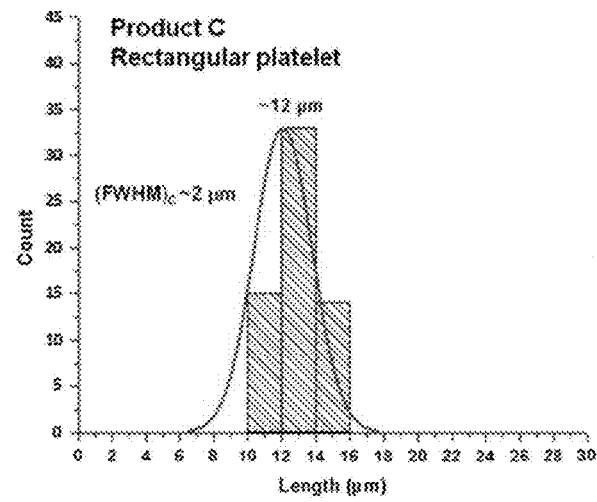
FIG. 7C shows the diameter distribution histograms of products C.
Figure 7D:
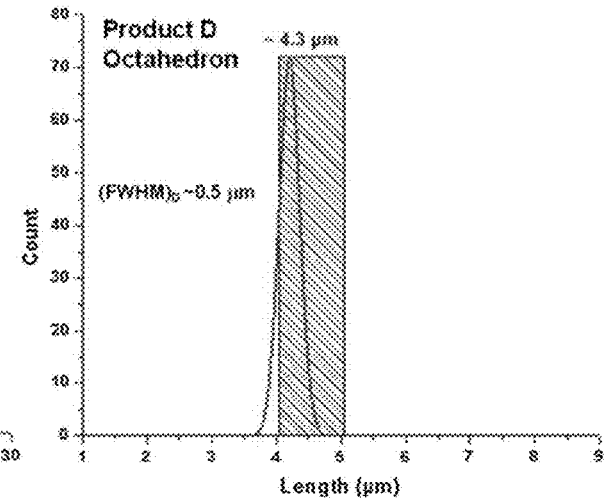
FIG. 7D shows the diameter distribution histograms of products D.

Product C is obtained by the solvothermal method described herein using the solvent polyethylene glycol. It was characterized by SEM and TEM and the results are shown in FIGS. 4a-4d. It is evident from FIGS. 4a and b that the product is comprised of rectangular disc like particles. The rectangular disc like particles tends to interlink together in layers and this layer-by-layer assembly leads to different morphologies as shown in FIGS. 4c and 4d. The diameter of these rectangular disc like particles lie in the range of 10 to 20 μm in length and 8-12 μm in width. The thickness of these particles is approximately 5 μm (FIG. 4c). The layer-by-layer assembly of these particles leads to the multilayer thickness and also responsible for the irregular edges. Some of these particles interlink together to form a flower like three dimensional morphology, indicated by red arrow in FIG. 4d. These discs like particles diffused together at the base and are separated from the front just like petals of flowers. The addition of further platelets to the cross leads to the flower shown at the red arrow head in FIG. 4b. The layer-by-layer arrangement of the platelets develops to the flower-like morphology shown in FIG. 4d. The edges of the flower shape $Fe_3O_4$ are very similar to that of original flowers and some of the platelets oriented upwards acts as stamens (the middle portion of original flowers). There are two possible explanations for the formation of the rectangular platelet of product C. The first is that flower-like structures are formed, and broken down to the rectangular layer by layer assembled platelets as the temperature rises in the solvothermal method. The other possibility is that the rectangular platelets are formed and arranged in a specific pattern to give rise to flower like structure. The morphology of the majority of product C is the micro rectangular platelet.

Product D: Octahedron of $Fe_3O_4$.

The product D was obtained by using n-hexane in the solvothermal method. The morphology of product D was characterized by SEM. The results are shown in FIGS. 5a-5d indicating polyhedron morphology. The product consists of uniform sized octahedra microparticles with eight distinct faces. Some of particles are not aggregated, see FIG. 5a. FIG. 5b shows some others are in aggregated form of the octahedra particles which are aligned together in the form of long cylinder.

The size of the octahedra is uniform throughout the product with no variations. The length of the side of the triangle of the octahedron is approximately 2.5 μm and the average diameter from one end to the other is about 4.3 μm. Some nanometer sized particles attached on the surface of the micro octahedron are observed in SEM micrograph FIG. 5c. The micro octahedra appear to be very compact and rigid from the outer and inner surfaces. The edges of the octahedron are uniform and distinct without irregularities.

It might be some cubic shaped particles that appeared first further grow towards the edges (each face of polyhedron). The lattice cell appearing at the initiation of the reaction and solvent molecule surrounds it in a specific pattern that facilitates its growth to an octahedral micro particles. Based on the fact that n-hexane is utilized as solvent in solvothermal synthesis support, an octahedral morphology may be identified.

Product E: Irregular Morphology of $Fe_3O_4$.

A mixture of 1:1 (v/v) n-hexane and ethylene glycol was used in the solvothermal method to obtain product E. The product has been characterized by SEM and TEM and the results are shown in FIGS. 6a-6d. The SEM results shows some of the particles are irregular shaped embedded in some of the material. At low SEM resolution, it is not possible to differentiate between different shapes in the product. The TEM results shown in FIGS. 6c and 6d show irregular shaped particles of few micrometers in diameter. Some of the particles are connected like a net and run to several micrometers in length. In addition to the big particles, there are a large number small particles

TABLE 2

Summary of various parameters obtained from XRD pattern analysis of products A-E

| Parameter | Product C and D | Product A and B |
|---|---|---|
| Name of compound | Magnetite | Magnetite |
| JCPDS no. | 19-0629 | 28-0491 |
| Crystal system | Cubic | Monoclinic |
| Type | Face centered | Primitive |
| Space group | Fd-3m (227) | P12/ml (10) |
| Crystallite size (A) | 282 | 282 |
| Cell parameters | | |
| a, b and c (Å) | 8.3851, 8.3851 and 8.3851 | 5.9444, 5.9247 and 8.3875 |
| α, β and γ(°) | 90.0, 90.0 and 90.0 | 90.0, 90.237° and 90.0 |
| Atom coordinates | | |
| x, y and z of iron | 0.125, 0.125 and 0.125 | 0.750, 0.500 and 0.125 |
| | 0.500, 0.500 and 0.500 | 0.000, 0.500 and 0.000 |
| | | 0.250, 0.250 and 0.250 |
| | | 0.000, 0.000 and 0.500 |
| | | 0.500, 0.500 and 0.000 |
| | | 0.500, 0.000 and 0.500 |
| | | 0.750, 0.000 and 0.125 |
| x, y and z of oxygen | 0.253, 0.253 and 0.253 | 0.250, 0.260 and 0.005 |

TABLE 2-continued

Summary of various parameters obtained from
XRD pattern analysis of products A-E

| Parameter | Product C and D | Product A and B |
|---|---|---|
| | | 0.510, 0.500 and 0.755 |
| | | 0.250, 0.240 and 0.495 |
| | | 0.010, 0.000 and 0.255 |
| | | 0.510, 0.000 and 0.745 |
| | | 0.010, 0.500 and 0.245 |
| No. of formula units per unit cells (Z) | 8.0 | 4.0 |
| Density (g/cm$^3$) | 5.21600 | 5.2060 |
| Volume (Å$^3$) | 591.9 | 225.6 |
| Spacing ($d_{hkl}$) (Å), 2-theta (°) and miller indices (hkl) | 4.84743, 18.286 and (111) | 5.43, 16.310 and (010) |
| | 2.96843, 30.079 and (220) | 4.05653, 21.892 and (100) |
| | 2.53149, 35.429 and (311) | 2.88045, 31.021 and (101) |
| | 2.42372, 37.061 and (222) | 2.715, 32.963 and (020) |
| | 2.09900, 43.058 and (400) | 2.69153, 33.259 and (002) |
| | 1.9261, 47.144 and (331) | 2.59659, 34.513 and (102) |
| | 1.71383, 53.416 and (422) | 2.20488, 40.895 and (121) |
| | 1.61581, 56.942 and (333) | 1.78442, 51.147 and (212) |
| | 1.48422, 62.527 and (440) | 1.74586, 52.361 and (201) |
| | 1.41918, 65.743 and (531) | 1.65292, 55.551 and (130) |
| | 1.39933, 66.797 and (442) | 1.63239, 56.311 and (131) |
| | 1.32752, 70.934 and (620) | 1.39209, 67.190 and (212) |
| | 1.28038, 73.969 and (533) | 1.3575, 69.141 and (040) |
| | 1.26574, 74.970 and (622) | 1.34287, 70.004 and (132) |
| | | 1.30996, 72.033 and (123) |
| | | 1.28733, 73.504 and (140) |
| | | 1.27756, 74.160 and (141) |
| | | 1.24264, 76.613 and (124) |
| | | 1.23355, 77.282 and (301) |
| | | 1.21037, 79.047 and (320) |

Effect of Solvent Nature and Composition on the Diameter and Diameter Distribution of Products.

FIGS. 7A-7D show the diameter distribution histograms of products A-D. The particle diameter of the products increases in the order: A<B<C<D<E. Non-polar solvent n-hexane was used for synthesis of product E while polar solvent ethylene glycol was used for synthesis of product A. The polarity of the solvent used during synthesis decreases from product A to D. It appears that smaller particles sizes are synthesized using polar solvents, whereas particles of larger diameters are synthesized using non-polar solvents. The diameter distribution of products A-D can be compared from FIGS. 7A-7D. Diameter distribution histogram of product E is not given because product E possess irregular reef like structures (see FIG. 6). All the diameters distribution histograms obeyed Gaussian distribution and possess one peak only indicating that the diameters of particles of products A-D vary in a specific range only. Also, it shows that particles of products A-D possess homogenous diameter distribution indicating that products A-D are monodisperse. In addition, the full width at half maxima (FWHM) values of the products were calculated and shown in FIGS. 7A-7D. FWHM value of product A and B can be compared with each because both products contain particles above 100 nm. Similarly FWHM value of product C and D can be compared with each other because both products contain particles below 100 μm. The value of FWHM for product B is smaller than that of product A indicating that product B has narrower diameter distribution than that of product A. This is due to the lesser polarity of the solvent used to produce product A than that of product B. Mixture of two solvents (ethylene glycol and water) was used for synthesis of product B while pure ethylene glycol was used for synthesis of product A. Microparticles of product B was synthesized on oil-water interface, that's why product B possess narrower distribution than that of product A. On the other hand, value of FWHM for product D is smaller than that of product C because polarity of solvent used for synthesis of product D is less than that of product C. The graphs of diameter distribution are compared from their respective value of FWHM. It means diameter of particles decreases with increase in polarity while FWHM value increases with increase in polarity. If smaller size is obtained then size distribution becomes large and if narrow size distribution is achieved then diameter of particles become greater.

Example 4

Figure 8A:
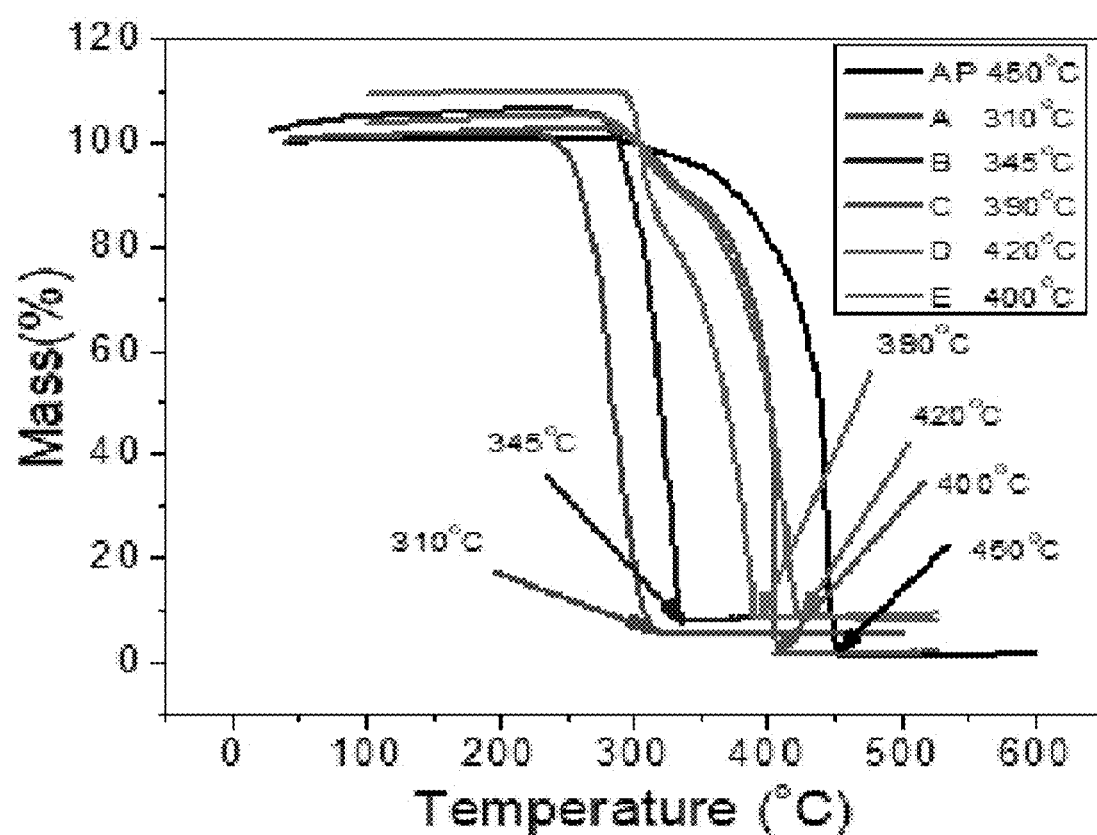
FIG. 8a shows TG observations of decomposition of AP in the presence of Fe₃O₄ particles of products A-E.

Thermal Decomposition of AP Catalyzed by Ferric Oxide Preparations A-E:

FIG. 8a shows the thermogravimetric results of the decomposition of AP-catalyzed by the ferric oxide preparations A-E and compared to the uncatalyzed reaction. Thermal decomposition temperature of pure AP is 450° C. It is observed that products A-E of ferric oxide have displayed catalytic activity. The thermal degradation of AP is based on a proton transfer mechanism. The degradation of the AP is initiated by the transfer of a proton from ammonium ion to perchlorate ion. The thermal energy provides the required energy to overcome the high energy barrier for the thermodynamically unfavored proton transfer step. The $Fe_3O_4$ nano/micro particles facilitate the charge transfer step by lowering the energy barrier. Identical mechanism has been proposed by Chaturvedi et al. ["A review on the use of nanometals as catalysts for the thermal decomposition of ammonium perchlorate." (2013) J Saudi Chem Sac 17:135-149] and Dey et al. ["Graphene-iron oxide nanocomposite (GINC): an efficient catalyst for ammonium perchlorate (AP) decomposition and burn rate enhancer for AP based composite propellant." (2015) RSC Adv 5:1950-1960] for the thermal degradation of AP in the presence of metals.

The porous hollow spheres of catalyst A having almost 140 nm diameter are proved to be the most effective among catalysts A-E. The results in Table 1 and FIG. 8a show that the final decomposition temperature for the porous hollow spheres is 310° C. There is almost 140° C. reduction in thermal decomposition temperature of AP when porous hollow are used as catalyst compared to the uncatalyzed decomposition. The thermal decomposition curve for this process is very smooth without any irregularities. Among catalyst A-E, octahedral particles of catalyst D showed the lowest catalytic activity. The final decomposition temperature of AP is 420° C. in the presence of catalyst D. There is a decrease of 30° C. in the final thermal decomposition of AP. Table 1 summarizes the results of the thermal decomposition temperatures of AP for catalysts A-E.

Figure 8B:
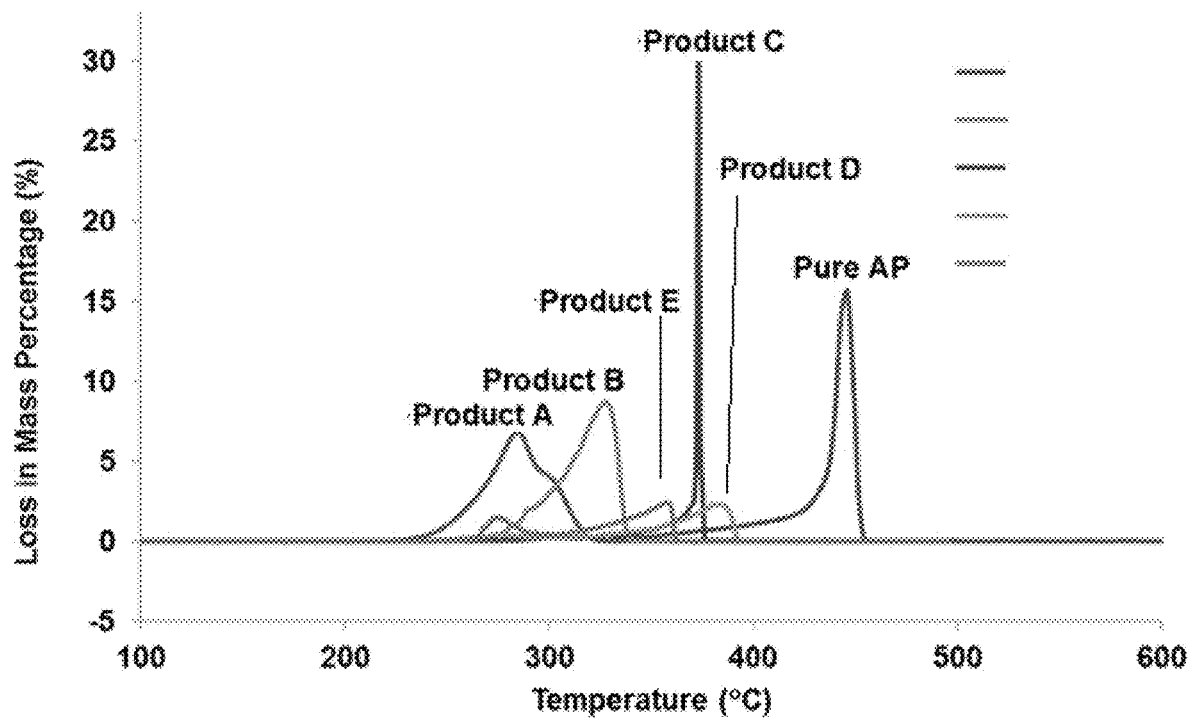
FIG. 8b shows temperature dependent plot of loss in mass percentage of AP in the presence of Fe₃O₄ particles of products A-E.

FIG. 8b shows the loss in mass percentage of AP versus temperature for the uncatalyzed and A-E catalyzed reactions. The extent of decomposition of AP is clearly shown in the figure. The figure shows that the temperature, at which maximum loss of mass percentage of AP has occurred, is different for different catalysts. Interestingly, the decomposition reaction-catalyzed by the micro rectangular platelets of catalyst C shows that all the mass of AP decomposed at once when temperature reached 373° C. In contrast, all other catalysts show much broader decomposition profiles (see FIG. 8b). The hollow microspheres of catalysts A and the microspheres B show well defined peaks at temperature 329 and 286° C., respectively. But catalysts D and E show no peak and continuous decrease in mass of AP over the whole temperature range (see FIG. 8b). Among all catalysts, catalyst A shows maximum decrease in thermal decomposition temperature of AP, and catalyst C shows sharp loss in mass percentage of AP at temperature 373° C. Diameter of particles of catalyst A is the smallest among all catalysts and it shows good catalytic activity. Hence, product A can be considered as a best catalyst among all the synthesized catalysts.

Example 5

Figure 9A:
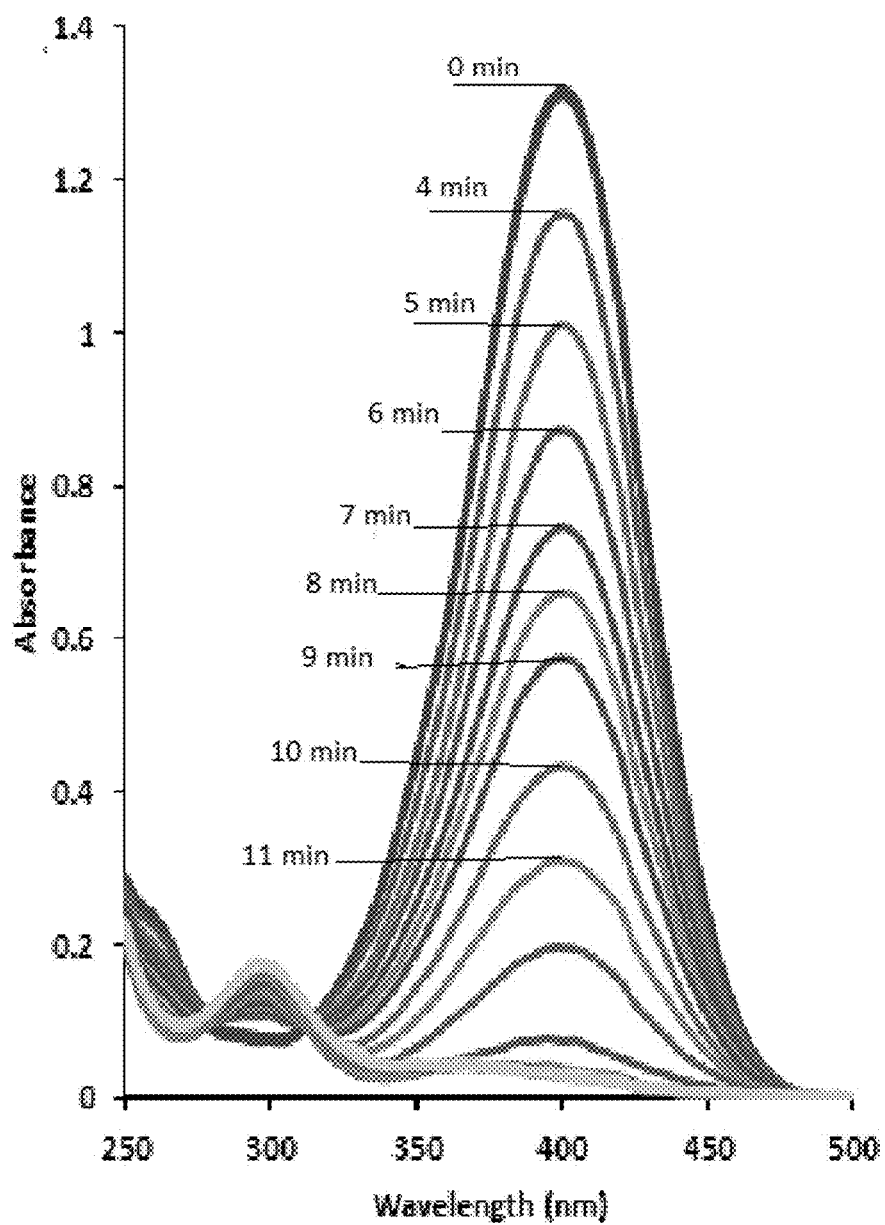
FIG. 9a shows a time dependent UV—Visible spectra of reduction of 4-NP catalyzed by product A in aqueous medium [conditions: [4-NP]=80 µM, [NaBH₄]=8 mM, [Fe₃O₄]=1 µg/L and temperature=22° C.
Figure 9B:
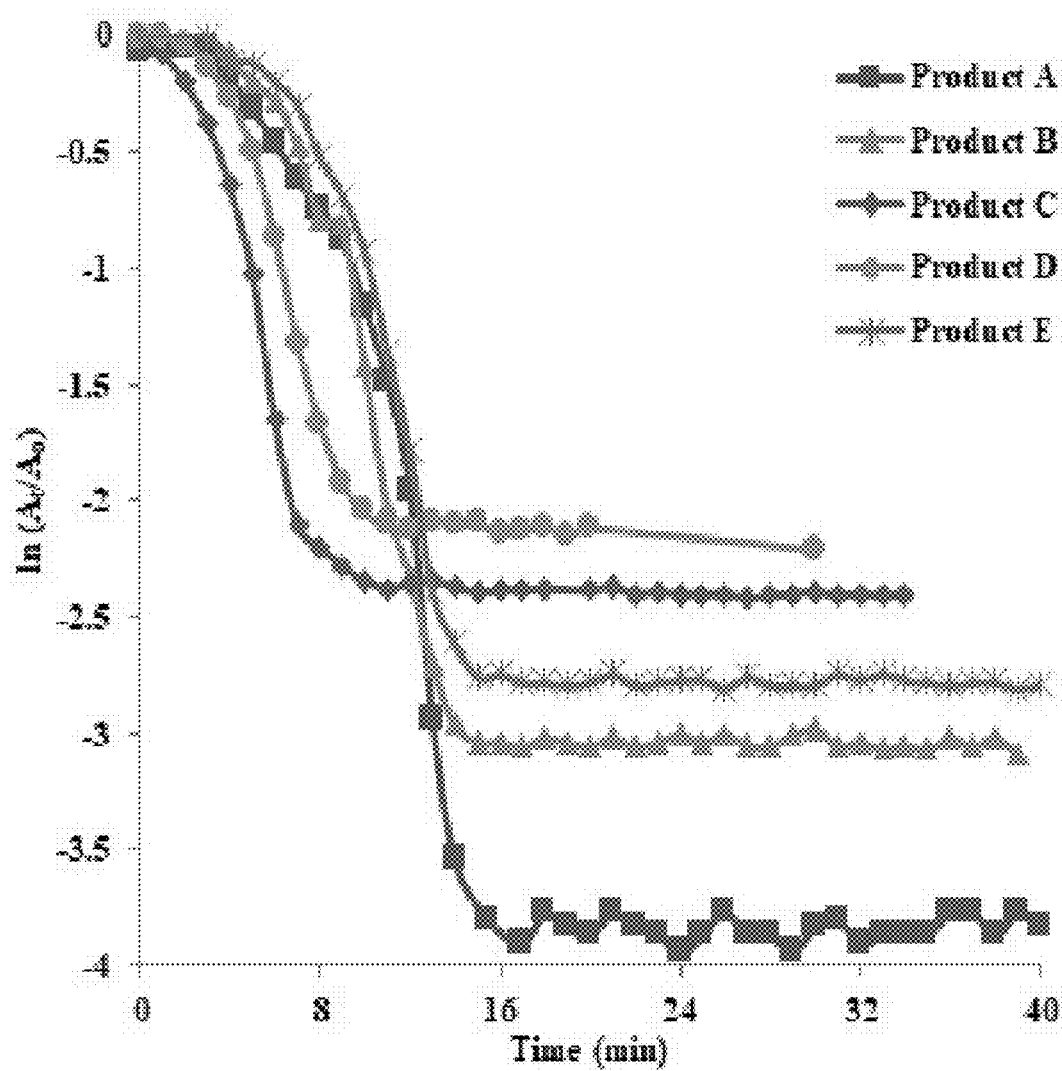
FIG. 9b shows plots of ln($A_t/A_0$) versus time for reduction of 4-NP catalyzed by product A-E [conditions: [4-NP]=80 µM, [NaBH₄]=8 mM, [Fe₃O₄]=1 µg/L and temperature=22° C.].
Figure 10:
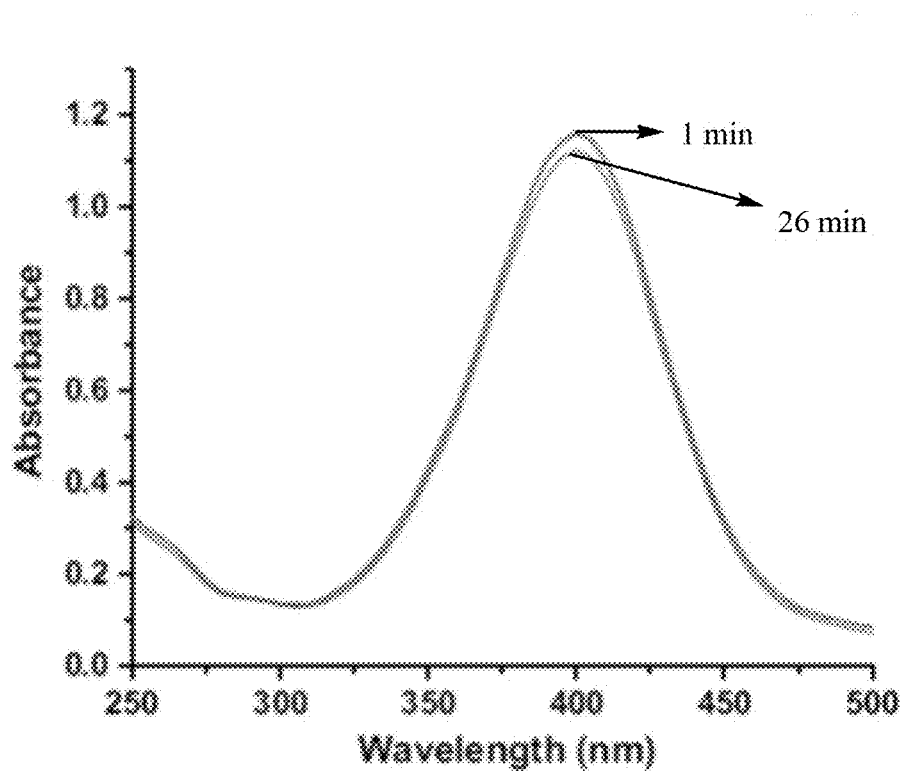
FIG. 10 shows a Time dependent UV—Visible spectra of reduction of 4-NP in the absence of catalyst [conditions: [4-NP]=80 µM, [NaBH₄]=8 nM and temperature=22° C.].

Catalytic Reduction of p-Nitrophenol (4-NP):

Reduction of 4-NP in aqueous media is used as a model to examine the catalytic activity of $Fe_3O_4$ micro/nanoparticles in wet media. $Fe_3O_4$ nano/microparticles catalyzed the reduction of 4-NP into 4-aminophenol (4-AP). Time dependent UV-Vis spectra of the reduction of 4-NP by sodium borohydride-catalyzed by ferric oxide hollow microsphere of product A is shown in FIG. 9a. FIG. 10 shows the time dependent UV-Vis spectrum of the same reaction mixture without the ferric oxide nano/microparticles. Comparison of FIGS. 9a and 10 clearly show the catalytic activity of the ferric oxide nano/microparticles. The observation of two isosbestic points in the results shown in FIG. 9a indicates that the p-nitrophenol is converted to p-aminophenol without accumulation of any reaction intermediate. Since Amax for 4-NP and 4-AP are 400 and 300 nm, respectively, [Farooqi et al. "Effect of acrylic acid feed contents of microgels on catalytic activity of silver nanoparticles fabricated hybrid microgels." (2015) Turk J Chem 39:96-107], the reduction of 4-NP is observed by following the UV-Vis spectral change with time. A first-order plot of ln $(A_t/A_0)$ vs time is non-linear and appears as a sigmoidal curve. The initial phase is characterized by slow acceleration phase (induction phase) of the reaction followed by rapid reaction phase and a termination phase, see FIG. 9b. A pseudo first order rate constants ($k_{app}$) were calculated from the straight line portion of the second phase of the reactions and the results are summarized in Table 1. The values of $k_{app}$ are in the following order: A>B>C>D>E. This is probably due to the difference in the ferric oxide particles diameter and morphology. The diameter of ferric oxide particles decreases in the following order: A<B<C<D<E. It is well-known that catalysis is a surface phenomenon. The surface area of particles decreases with increasing the diameter. So, it appears that the total surface area of the particles increases with decreasing the diameter of individual particle. The value of $k_{app}$ for the reduction catalyzed the porous hollow spheres by catalyst A is greatest among all the products. Product A is porous and possesses very small diameter, so it provides very large surface area for catalysis. The value of $k_{app}$ of catalysts D and E is almost the same because their sizes are almost the same, which confirms dependency of $k_{app}$ on the particles diameter.

The present disclosure describes a method of preparation of $Fe_3O_4$ nano/microparticles with a predominant morphology such as nanosphere, microsphere, spherical aggregates, octahedral, irregular structure, and/or microrectangular plates. The different morphologies observed result from changing the solvent used in the method preparation. Most products of the method are uniform in shape and diameter distribution, are well separated from each other, and are hollow from the inside with thin and defined boundaries. The nano/microparticles are catalysts for the decomposition of ammonium perchlorate (AP) and the reduction of nitro compounds to the corresponding amines. The results show that the catalysts have good surface properties. $Fe_3O_4$ catalysts show a trend in catalytic thermal decomposition of AP; with an increase in the diameter of $Fe_3O_4$ particles, the catalytic properties gradually decrease and particles with 140 nm diameter decrease the decomposition temperature by 140° C. Also, the temperature at which maximum loss in mass percentage of AP occurred was investigated. All the AP decomposed at once at 373° C. when a catalyst with a micro rectangular platelet predominant morphology was used. Products A-E catalyzed the continuous decomposition of AP over the complete range of temperature. Also, all of the prepared nano/microparticles were used as catalysts for reduction of 4-nitrophenol. It was observed that the value of $k_{app}$ of the reduction is the largest for hollow microsphere morphology and the smallest for a catalyst having a rectangular platelet morphology. It was also observed that value of $k_{app}$ decreased with increase in diameter of the particles. The above results have shown that these catalysts can be efficiently used for dry as well as wet processes.

The invention claimed is:

1. A method, comprising:
   heating a composition comprising a ferric halide and an alkali metal salt of a carboxylic acid in hexane at a temperature of 150-300° C. in a sealed container to form ferric oxide microparticles; and
   contacting an ammonium salt with the ferric oxide microparticles,
   wherein the ferric oxide microparticles have an octahedron morphology,
   wherein on the contacting the ammonium salt is decomposed, and
   wherein the ammonium salt has a final decomposition temperature of 420° C.

2. The method of claim 1, wherein the ferric halide is ferric chloride.

3. The method of claim 1, wherein the alkali metal salt of a carboxylic acid is sodium acetate.

4. The method of claim 1, wherein the heating temperature is in the range of about 195 to 205° C.

5. The method of claim 1, wherein the composition consists of a ferric halide and an alkali metal salt of a carboxylic acid in hexane.

6. The method of claim 1, wherein a particle diameter of the ferric oxide microparticles catalyst is about 4.3 μm.

7. The method of claim 1, wherein the ferric halide is selected from the group consisting of ferric fluoride, ferric chloride, ferric bromide, and ferric iodide.

8. The method of claim 1, wherein the carboxylic acid of the alkali metal salt of a carboxylic acid is selected from the group consisting of formic acid, acetic acid, propionic acid, butyric acid, citric acid, oxalic acid, and tartaric acid.

9. The method of claim 1, wherein the composition is heated for 8 to 36 hours.

10. The method of claim 1, wherein the composition is heated for 12 to 24 hours.

11. The method of claim 1, wherein the composition does not comprise a templating agent.

12. The method of claim 1, wherein the ferric oxide microparticles are aggregated.

13. The method of claim 12, wherein aggregates of the aggregated ferric oxide microparticles are in a form of a cylinder.

\* \* \* \* \*